United States Patent
Selbo

(10) Patent No.: US 8,933,088 B2
(45) Date of Patent: Jan. 13, 2015

(54) CRYSTALLINE FORMS OF 3-[5-CHLORO-4-[(2,4-DIFLUOROBENZYL) OXY]-6-OXOPYRIMIDIN- 1(6H)-YL]-N-(2-HYDROXYETHYL)-4-METHYLBENZAMIDE

(71) Applicant: Pharmacia & Upjohn Company LLC, Kalamazoo, MI (US)

(72) Inventor: Jon G. Selbo, Wentzville, MO (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/669,564

(22) Filed: Nov. 6, 2012

(65) Prior Publication Data

US 2013/0158053 A1 Jun. 20, 2013

Related U.S. Application Data

(62) Division of application No. 11/576,897, filed as application No. PCT/IB2005/003030 on Oct. 3, 2005, now Pat. No. 8,324,230.

(60) Provisional application No. 60/618,466, filed on Oct. 13, 2004.

(51) Int. Cl.
- *A01N 43/54* (2006.01)
- *A61K 31/505* (2006.01)
- *C07D 239/02* (2006.01)

(52) U.S. Cl.
USPC .......................................... 514/269; 544/319

(58) Field of Classification Search
USPC .......................................... 514/269; 544/319
See application file for complete search history.

(56) References Cited

U.S. PATENT DOCUMENTS

| | | | |
|---|---|---|---|
| 7,183,287 B2 | 2/2007 | Durley et al. | |
| 7,795,271 B2 | 9/2010 | Durley et al. | |
| 2004/0242608 A1 | 12/2004 | Durley | |

OTHER PUBLICATIONS

EPO Search Report, Application No. 13186682.4, dated Feb. 19, 2014; Publication No. 2708531.
Cohen, Philip, "The search for physiological substrates of MAP and SAP kinases in mammalian cells", Trends in Cell Biology, Sep. 1997, pp. 353-361, vol. 7.
Zhao, Ming, et al., "Regulation of the MEF2 Family of Transcription Factors by p38", Molecular and Cellular Biology, Jan. 1999, pp. 21-30, 19(1).
Tanoue, Takuji, et al., "Identification of a docking groove on ERK and P38 MAP kinases that regulates the specificity of docking interactions", The Embo Journal, 2001, pp. 466-479, 20(3).
Paul, Andrew, et al., "Stress-activated Protein Kinases: Activation, Regulation and Function", Cell Signal, 1997, pp. 403-410, 9(6).
Lee, John C., et al., "A protein kinase involved in the regulation of inflammatory cytokine biosynthesis", Nature, Dec. 1994, pp. 739-745, 372(22/29).
MacKay, Katrina, et al., "An Inhibitor of p38 Mitogen-activated Protein Kinase Protects Neonatal Cardiac Myocytes from Ischemia", The Journal of Biological Chemistry, 1999, pp. 6272-6279, 274(10).
Underwood, David, et al., "SB 239063, a Potent p38 MAP Kinase Inhibitor, Reduces Inflammatory Cytokine Production, Airways Eosinophil Infiltration, and Persistence", The Journal of Pharmacology and Experimental Therapeutics, 2000, pp. 281-288, 293(1).
Boehm, Jeffrey, et al., "New inhibitors of p38 kinase", Expert Opinion on therapeutic Patents, 2000, pp. 25-37, 10 (1).
Dinarello, Charles, "Interleukin-1", Reviews of Infectious Diseases, Jan.-Feb. 1984, pp. 51-95, 6(1).
Brahn, E., et al., "Effects of Tumor Necrosis Factor Alpha (TNF-α) on Collagen Arthritis", Lymphokine and Cytokine Research, 1992, pp. 253-256, 11(5).
Cooper, W.O., et al., "Acceleration of onset of collagen-induced arthritis by intra-articular injection of tumour necrosis factor or transforming growth factor-beta", Clinical Experimental Immunology, 1992, pp. 244-250, vol. 89.
Perretti, M., et al., "Serum corticosterone, interleukin-1 and tumour necrosis factor in rat experimental endotoxaemia: comparison between Lewis and Wistar strains", British Journal of Pharmacology, 1993, pp. 868-874, vol. 110.
Database WPI; Section Ch., Week 198643; Derwent Publications Ltd., London, GB; AN 1986-281625, XP002294127.
Datebase CHEMABS Online! Chemical Abstracts Service, Columbus, OH, US; XP002294080, retrieved from STN Database accession No. 1966:104220 abstract; and XP002294078.
Whitehead, Calvert W., et al., "Exchange amination. Alkyl and Arylamino-pyrimidines and Purines", Journal of the American Chemical Society, Aug. 5, 1960, pp. 3791-3974, vol. 82.
Goldner, H., et al., "Eine Neue Xanthin-Synthese", Justus Liebigs Annalen Der Chemie, Verlag Chemie, Weinheim, DE., 1966, pp. 142-158, vol. 691.
Stuart, John M., et al., "Collagen Autoimmune Arthritis", Annual Review Immunology, 1984, pp. 199-218, vol. 2.

*Primary Examiner* — Paul V. Ward
(74) *Attorney, Agent, or Firm* — Martha G. Munchhof

(57) ABSTRACT

Crystalline forms of the p38 kinase inhibitor 3-[5-chloro-4-[(2,4-difluorobenzyl)oxy]-6-oxopyrimidin-1(6H)-yl]-N-(2-hydroxyethyl)-4-methylbenzamide is provided. Also provided are combinations and pharmaceutical compositions comprising the crystalline forms, and methods for the prophylaxis and/or treatment of a p38 kinase-mediated condition comprising administering to a subject a therapeutically effective amount of the crystalline forms.

16 Claims, 13 Drawing Sheets

CRYSTALLINE FORMS OF 3-[5-CHLORO-4-[(2,4-DIFLUOROBENZYL) OXY]-6-OXOPYRIMIDIN-1(6H)-YL]-N-(2-HYDROXYETHYL)-4-METHYLBENZAMIDE

CROSS REFERENCE TO RELATED APPLICATIONS

This application is a divisional of U.S. patent application Ser. No. 11/576,897, filed on Feb. 20, 2008, which is a U.S. National Stage of International Patent Application Number PCT/IB2005/003030, filed on Oct. 3, 2005, which claims priority from U.S. Provisional Application Ser. No. 60/618,466, filed Oct. 13, 2004, the disclosure of each of which is incorporated herein by reference in its entirety.

FIELD OF THE INVENTION

This invention is in the field of pharmaceutical agents active as p38 kinase inhibitors, and more particularly concerns the p38 kinase inhibitor 3-[5-chloro-4-[(2,4-difluorobenzyl)oxy]-6-oxopyrimidin-1(6H)-yl]-N-(2-hydroxyethyl)-4-methylbenzamide. Specifically, the invention relates to a novel forms of 3-[5-chloro-4-[(2,4-difluorobenzyl)oxy]-6-oxopyrimidin-1(6H)-yl]-N-(2-hydroxyethyl)-4-methylbenzamide.

BACKGROUND OF THE INVENTION

The compound 3-[5-chloro-4-[(2,4-difluorobenzyl)oxy]-6-oxopyrimidin-1(6H)-yl]-N-(2-hydroxyethyl)-4-methylbenzamide having the structure (1) below (referred to herein as "Compound 1") is described in U.S. patent application Ser. No. 10/808,146 (filed Mar. 24, 2004) discloses a class of substituted pyrimidinone compounds and related pharmaceutical compositions that are useful for the treatment and/or prophylaxis of a p38 kinase-mediated condition, example of such include inflammation and inflammation related conditions.

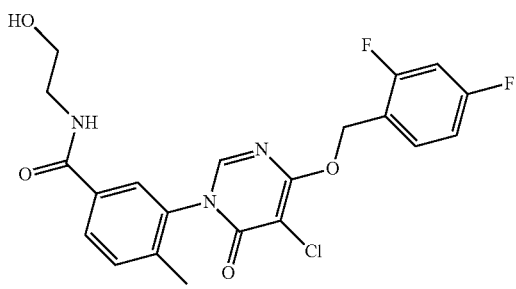

A need exists for a crystalline form of Compound 1 that is physically stable and sufficiently bioavailable, and for reliable and reproducible processes for the manufacture and/or purification of such crystalline form. There is now provided novel crystalline forms of Compound 1 having a high degree of physical stability at common temperatures of storage and use.

SUMMARY

The invention provides, in a first aspect, an anhydrous crystalline form of Compound 1 ("Form A").

In another aspect, the invention provides pharmaceutical compositions comprising Form A, and further optionally comprising one or more pharmaceutically acceptable excipients.

In another aspect, the invention provides pharmaceutical compositions containing about 0.1 mg to about 1000 mg of Form A.

In another aspect, the invention provides a method for prophylaxis and/or treatment of an inflammatory condition comprising administering to a subject a therapeutically effective amount of Form A.

The invention provides, in a second aspect, a hydrous crystalline form of Compound 1 ("Form B").

In another aspect, the invention provides pharmaceutical compositions comprising Form B, and further optionally comprising one or more pharmaceutically acceptable excipients.

In another aspect, the invention provides pharmaceutical compositions containing about 0.1 mg to about 1000 mg of Form B.

In another aspect, the invention provides a method for prophylaxis and/or treatment of an inflammatory condition comprising administering to a subject a therapeutically effective amount of Form B.

Additional aspects of the invention will be in part apparent and in part pointed out throughout this application.

DETAILED DESCRIPTION

Figure 1:
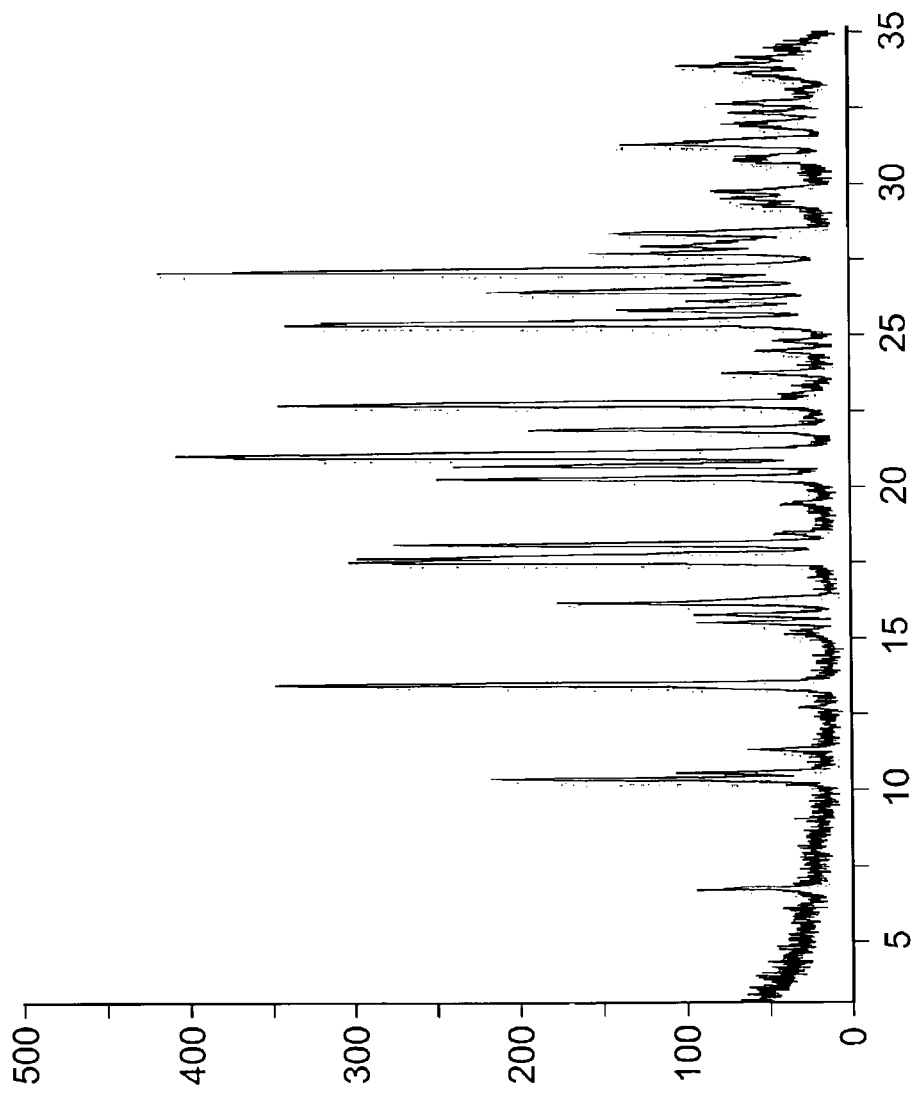
FIG. 1 shows an illustrative X-ray powder diffraction pattern for Form A.

The present invention relates to crystalline forms of 3-[5-chloro-4-[(2,4-difluorobenzyl)oxy]-6-oxopyrimidin-1(6H)-yl]-N-(2-hydroxyethyl)-4-methylbenzamide.

Polymorphs are different crystalline forms of the same compound. Different crystalline forms can have different physical properties such as different melting point, powder x-ray and solid state NMR. The present invention relates to three different crystalline forms of 3-[5-chloro-4-[(2,4-difluorobenzyl)oxy]-6-oxopyrimidin-1(6H)-yl]-N-(2-hydroxyethyl)-4-methylbenzamide.

More specifically, the present invention provides an anhydrous crystalline form of Compound 1 ("Form A").

The invention provides, in a second aspect, a hydrous crystalline form of Compound 1 ("Form B").

The invention provides, in a third aspect, a hydrous crystalline form of Compound 1 ("Form C").

As with other pharmaceutical compounds and compositions, the chemical and physical properties of 3-[5-chloro-4-[(2,4-difluorobenzyl)oxy]-6-oxopyrimidin-1(6H)-yl]-N-(2-hydroxyethyl)-4-methylbenzamide. ("Compound 1") are important in its commercial development. These properties include, but are not limited to: (1) packing properties such as molar volume, density and hygroscopicity, (2) thermodynamic properties such as melting temperature, vapor pressure and solubility, (3) kinetic properties such as dissolution rate and stability (including stability at ambient conditions, especially to moisture, and under storage conditions), (4) surface properties such as surface area, wettability, interfacial tension and shape, (5) mechanical properties such as hardness, tensile strength, compactibility, handling, flow and blend, (6) filtration properties, (7) chemical purity, and (8) physical and chemical stability. These properties can affect, for example, processing and storage of pharmaceutical compositions comprising Compound 1. Solid-state forms of Compound 1 that provide an improvement in one or more of these properties relative to other solid-state forms of Compound 1 are desirable.

According to the present invention, therefore, a new solid-state form of Compound 1 has been discovered. The specific solid-state form of Compound 1 that has been discovered includes an anhydrous crystalline form possessing thermodynamic stability under normal manufacturing conditions.

In one embodiment, the invention comprises the Form A of Compound 1. The Form A possesses physical stability at ambient temperatures. Solid-state forms of Compound 1 that do not require special processing or storage conditions, and that avoid the need for frequent inventory replacement, such as Form A, are desirable. For example, selection of a solid-state form of Compound 1 that is physically stable during a manufacturing process (such as during milling of Compound 1 to obtain a material with reduced particle size and increased surface area) can avoid the need for special processing conditions and the increased costs generally associated with such special processing conditions. Similarly, selection of a solid-state form of Compound 1 that is physically stable over a wide range of storage conditions (especially considering the different possible storage conditions that can occur during the lifetime of a Compound 1 product) can help avoid polymorphic or other degradative changes in the Compound 1 that can lead to product loss or deterioration of product efficacy. Therefore, the selection of a solid-state form of Compound 1 such as Form A having greater physical stability provides a meaningful benefit over less stable Compound 1 solid-state forms.

Indications

The solid-state form of Compound 1 described in this application is useful for, but not limited to, the treatment of any condition in a human, or other mammal, which is exacerbated or caused by excessive or unregulated cytokine production by the mammal, such as TNF or p38 kinase production. The solid-state forms of Compound 1 is p38 kinase antagonists, directly or indirectly antagonize cytokines such as TNF and IL-1 proteins, and/or have the ability to retard the natural course of joint destruction in rheumatoid arthritis patients. Accordingly, the present invention provides a method of treating a cytokine-mediated condition, which comprises administering to a subject an effective cytokine-interfering amount of a solid-state form of Compound 1.

The solid-state form of Compound 1 is useful for, but not limited to, the treatment or prophylaxis of:

(1) inflammation;
(2) arthritis including rheumatoid arthritis, spondyloarthropathies, gouty arthritis, osteoarthritis, systemic lupus erythematosus and juvenile arthritis, osteoarthritis, and other arthritic conditions;
(3) neuroinflammation;
(4) allergy, Th2 mediated diseases;
(5) pain (i.e., use as an analgesic) including but not limited to neuropathic pain;
(6) fever (i.e., use as an antipyretic);
(7) pulmonary disorders or lung inflammation, including adult respiratory distress syndrome, pulmonary sarcoidosis, asthma, silicosis, chronic pulmonary inflammatory disease, chronic obstructive pulmonary disease (COPD), and asthma;
(8) cardiovascular diseases including atherosclerosis, myocardial infarction (including post-myocardial infarction indications), thrombosis, congestive heart failure, and cardiac reperfusion injury, as well as complications associated with hypertension and/or heart failure such as vascular organ damage, restenosis;
(9) cardiomyopathy;
(10) stroke including ischemic and hemorrhagic stroke;
(11) ischemia including brain ischemia and ischemia resulting from cardiac/coronary bypass;
(12) reperfusion injury
(13) renal reperfusion injury;
(14) brain edema;
(15) neurotrauma and brain trauma including closed head injury;
(16) neurodegenerative disorders;
(17) central nervous system disorders (including, but not limited to, central nervous system disorders having an inflammatory or apoptotic component), such as Alzheimer's disease, Parkinson's disease, Huntington's Disease, amyotrophic lateral sclerosis, spinal cord injury, and peripheral neuropathy.
(18) liver disease and nephritis;
(19) gastrointestinal conditions such as inflammatory bowel disease, Crohn's disease, gastritis, irritable bowel syndrome and ulcerative colitis;
(20) ulcerative diseases such as gastric ulcer;
(21) periodontal disease
(22) ophthalmic diseases such as retinitis, retinopathies (including diabetic retinopathy), uveitis, ocular photophobia, nonglaucomatous optic nerve atrophy, and age related macular degeneration (ARMD) (including ARMD-atrophic form);
(23) ophthalmological conditions such as corneal graft rejection, ocular neovascularization, retinal neovascularization including neovascularization following injury or infection, and retrolental fibroplasia;
(24) glaucoma including primary open angle glaucoma (POAG), juvenile onset primary open-angle glaucoma, angle-closure glaucoma, pseudoexfoliative glaucoma, anterior ischemic optic neuropathy (AION), ocular hypertension, Reiger's syndrome, normal tension glaucoma, neovascular glaucoma, ocular inflammation and corticosteroid-induced glaucoma;
(25) acute injury to the eye tissue and ocular traumas such as post-traumatic glaucoma, traumatic optic neuropathy, and central retinal artery occlusion (CRAO);
(26) diabetes;
(27) diabetic nephropathy;
(28) skin-related conditions such as psoriasis, eczema, burns, dermatitis, keloid formation, scar tissue formation, and angiogenic disorders;
(29) viral and bacterial infections, including sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, and herpes virus;

(30) myalgias due to infection;
(31) influenza;
(32) endotoxic shock, sepsis;
(33) toxic shock syndrome;
(34) autoimmune disease including graft vs. host reaction and allograft rejections;
(35) treatment of bone resorption diseases, such as osteoporosis;
(36) multiple sclerosis;
(37) disorders of the female reproductive system such as endometriosis;
(38) pathological, but non-malignant, conditions such as hemaginomas, including infantile hemaginomas, angiofibroma of the nasopharynx and avascular necrosis of bone;
(39) benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovarian cancer, cervical cancer, lung cancer, breast cancer and skin cancer, such as squamous cell and basal cell cancers, prostate cancer, renal cell carcinoma, and other known cancers that affect epithelial cells throughout the body;
(40) leukemia;
(41) lymphoma;
(42) systemic lupus erthrematosis (SLE);
(43) angiogenesis including neoplasia; and
(44) metastasis.

The crystalline form of Compound 1 disclosed in this application is also useful for preventing the production or expression of cyclooxygenase-2, or cyclooxygenase-2 activity.

Definitions

The term "crystalline form" as applied to Compound 1 herein refers to a solid-state form wherein the Compound 1 molecules are arranged to form a distinguishable crystal lattice (i) comprising distinguishable unit cells, and (ii) yielding diffraction peaks when subjected to X-ray radiation.

The term "crystallization" as used herein can refer to crystallization and/or recrystallization depending upon the applicable circumstances relating to preparation of Compound 1 starting material.

The term "direct crystallization" as used herein refers to crystallization of Compound 1 directly from a suitable solvent without formation and desolvation of an intermediate solvated crystalline solid-state form of Compound 1.

The term "Compound 1 drug substance" as used herein means Compound 1 per se as qualified by the context in which the term is used, and can refer to unformulated Compound 1 or to Compound 1 present as an ingredient of a pharmaceutical composition.

The term "particle size" as used herein refers to particle size as measured by conventional particle size measuring techniques well known in the art, such as laser light scattering, sedimentation field flow fractionation, photon correlation spectroscopy or disk centrifugation. One nonlimiting example of a technique that can be used to measure particle size is a liquid dispersion technique employing a Sympatec Particle Size Analyzer. The "$D_{90}$ particle size" is a particle size such that 90% by weight of the particles are smaller than the $D_{90}$ particle size as measured by such conventional particle size measuring techniques.

The term "DSC" means differential scanning calorimetry.
The term "HPLC" means high pressure liquid chromatography.
The term "IR" means infrared.
The term "msec" means millisecond.
The term "purity" herein, unless otherwise qualified, means the chemical purity of Compound 1 according to conventional HPLC assay.
The term "phase purity" herein means the solid-state purity of Compound 1 with regard to a particular crystalline or amorphous form of the Compound 1 as determined by X-ray powder diffraction analytical methods described herein. The term "phase pure" refers to purity with respect to other solid-state forms of Compound 1 and does not necessarily imply a high degree of chemical purity with respect to other compounds.
The term "PXRD" means X-ray powder diffraction.
The term "TGA" means thermogravimetric analysis.

Characterization of Crystalline Forms A, B, and C

I. X-Ray Diffraction

Powder X-ray Diffraction (PXRD) was performed using a Broker D-8 Advance diffractometer (serial #002096) operating under DIFFRACplus 2000 and Microsoft Windows NT™ 4.0 software. The system used a copper X-ray source maintained at 40 kV and 40 mA to provide Cu K$\alpha_1$ (1.5406 Å) and Cu K$\alpha_2$ (1.54439 Å) radiation with an intensity weighted average of (K$\alpha_{ave}$) 1.54184 Å. A scintillation counter was used for detection. Beam aperture was controlled using primary 2° Soller slits and a fixed divergence slit of 2 mm. A diffracted beam monochromator was used to remove K$\beta$ radiation and fixed 2 mm anti-scatter, secondary 2° Soller slits, 0.2 mm monochromator, and 0.6 mm detector slits were employed. Data were collected using a step scan of 0.02° per point with a 0.1 second/point counting time over a range of 3 to 35° two-theta. Bruker Round, top loading, stainless steel sample cups or fabricated aluminum inserts held in Bruker plastic sample cup holders were utilized for all analyses. Samples were run as is or after light hand grinding.

Table 1 presents data obtained for a sample of Form A.

TABLE 1

X-Ray Diffraction Data

| Angle (2-theta degrees) | d-value | Intensity (Counts) | Intensity (%) |
| --- | --- | --- | --- |
| 6.74 | 13.111 | 78 | 18.7 |
| 10.38 | 8.515 | 214 | 51.2 |
| 10.59 | 8.347 | 88 | 21.1 |
| 11.34 | 7.799 | 63 | 15.1 |
| 13.49 | 6.559 | 344 | 82.3 |
| 15.2 | 5.825 | 27 | 6.5 |
| 15.51 | 5.708 | 87 | 20.8 |
| 15.78 | 5.611 | 95 | 22.7 |
| 16.18 | 5.473 | 170 | 40.7 |
| 17.58 | 5.041 | 299 | 71.5 |
| 17.68 | 5.013 | 297 | 71 |
| 18.11 | 4.893 | 275 | 65.8 |
| 18.47 | 4.799 | 46 | 11 |
| 19.46 | 4.557 | 40 | 9.6 |
| 20.3 | 4.371 | 248 | 59.3 |
| 20.73 | 4.281 | 238 | 56.9 |
| 21.08 | 4.21 | 385 | 92.1 |
| 21.9 | 4.055 | 193 | 46.2 |
| 22.76 | 3.904 | 345 | 82.5 |

TABLE 1-continued

X-Ray Diffraction Data

| Angle (2-theta degrees) | d-value | Intensity (Counts) | Intensity (%) |
| --- | --- | --- | --- |
| 23.76 | 3.742 | 77 | 18.4 |
| 24.48 | 3.634 | 57 | 13.6 |
| 24.8 | 3.587 | 40 | 9.6 |
| 25.43 | 3.5 | 336 | 80.4 |
| 25.85 | 3.444 | 140 | 33.5 |
| 26.15 | 3.405 | 98 | 23.4 |
| 26.48 | 3.363 | 211 | 50.5 |
| 26.87 | 3.316 | 86 | 20.6 |
| 27.16 | 3.28 | 418 | 100 |
| 27.73 | 3.214 | 156 | 37.3 |
| 27.96 | 3.189 | 125 | 29.9 |
| 28.38 | 3.142 | 144 | 34.4 |
| 29.31 | 3.044 | 62 | 14.8 |
| 29.52 | 3.023 | 79.9 | 19.1 |
| 29.76 | 2.999 | 80 | 19.1 |
| 30.82 | 2.899 | 68 | 16.3 |
| 31.33 | 2.852 | 137 | 32.8 |
| 31.98 | 2.797 | 76 | 18.2 |
| 32.34 | 2.766 | 72 | 17.2 |
| 32.66 | 2.74 | 68 | 16.3 |
| 33.64 | 2.662 | 68 | 16.3 |
| 33.91 | 2.642 | 100 | 23.9 |

Form A typically has an X-ray powder diffraction pattern comprising at least one peak selected from the group consisting of 13.5±0.2, 17.6±0.2, 17.7±0.2, 21.1±0.2, 22.8±0.2, 25.4±0.2, and 27.2±0.2 degrees 2 theta. In one embodiment of the invention, the solid-state form of Compound 1 is Form A having an X-ray powder diffraction pattern comprising peaks at 13.5±0.2, 21.1±0.2, 22.8±0.2, 25.4±0.2 and 27.2±0.2 degrees 2 theta. In another embodiment, the solid-state form of Compound 1 is Form A having an X-ray powder diffraction pattern comprising peaks at 13.5±0.2, 21.1±0.2 and 27.2±0.2 degrees 2 theta. In yet another embodiment a crystalline form of 3-[5-chloro-4-[(2,4-difluorobenzyl)oxy]-6-oxopyrimidin-1(6H)-yl]-N-(2-hydroxyethyl)-4-methylbenzamide having a melting point in a range from about 138.5° C. to about 142.5° C., and an X-ray powder diffraction pattern comprising peaks at 13.5±0.2, 21.1±0.2 and 27.2±0.2 degrees 2 theta.

FIG. 1 shows an illustrative X-ray powder diffraction pattern for Form A.

Table 2 presents data obtained for a sample of Form B.

TABLE 2

X-Ray Diffraction Data

| Angle (2-theta degrees) | d-value | Intensity (Counts) | Intensity (%) |
| --- | --- | --- | --- |
| 5.56 | 15.891 | 84 | 24.1 |
| 6.85 | 12.898 | 101 | 28.9 |
| 7.94 | 11.129 | 53 | 15.2 |
| 11.08 | 7.982 | 65 | 18.6 |
| 11.81 | 7.486 | 231 | 66.2 |
| 13.68 | 6.467 | 165 | 47.3 |
| 14.08 | 6.286 | 26 | 7.4 |
| 15.81 | 5.602 | 169 | 48.4 |
| 16.65 | 5.32 | 66 | 18.9 |
| 18.51 | 4.789 | 43 | 12.3 |
| 19.15 | 4.63 | 110 | 31.5 |
| 20.18 | 4.397 | 79 | 22.6 |
| 20.97 | 4.232 | 61 | 17.5 |
| 21.38 | 4.153 | 151 | 43.3 |
| 21.89 | 4.056 | 134 | 38.4 |
| 22.22 | 3.998 | 105 | 30.1 |
| 22.69 | 3.915 | 66 | 18.9 |
| 23.21 | 3.828 | 81 | 23.2 |
| 23.67 | 3.756 | 106 | 30.4 |

TABLE 2-continued

X-Ray Diffraction Data

| Angle (2-theta degrees) | d-value | Intensity (Counts) | Intensity (%) |
| --- | --- | --- | --- |
| 24.41 | 3.644 | 107 | 30.7 |
| 25.2 | 3.532 | 78 | 22.3 |
| 26.23 | 3.395 | 112 | 32.1 |
| 26.89 | 3.313 | 349 | 100 |
| 27.52 | 3.238 | 53 | 15.2 |
| 28.3 | 3.151 | 129 | 37 |
| 29.83 | 2.992 | 94 | 26.9 |
| 31 | 2.882 | 61 | 17.5 |
| 32.42 | 2.76 | 57 | 16.3 |
| 32.83 | 2.725 | 46 | 13.2 |
| 33.57 | 2.667 | 42 | 12 |
| 34.09 | 2.628 | 58 | 16.6 |

Form B typically has an X-ray powder diffraction pattern comprising at least one peak selected from the group consisting of 11.8±0.2, 13.7±0.2, 15.8±0.2, 21.4±0.2, 21.9±0.2, 26.2±0.2, and 26.9±0.2 degrees 2 theta. In one embodiment of the invention, the solid-state form of Compound 1 is Form B having an X-ray powder diffraction pattern comprising peaks at 11.8±0.2, 13.7±0.2, 15.8±0.2, 21.4±0.2 and 26.9±0.2 degrees 2 theta. In another embodiment, the solid-state form of Compound 1 is Form B having an X-ray powder diffraction pattern comprising peaks at 11.8±0.2, 15.8±0.2 and 26.9±0.2 degrees 2 theta. In yet another embodiment a crystalline form of 3-[5-chloro-4-[(2,4-difluorobenzyl)oxy]-6-oxopyrimidin-1(6H)-yl]-N-(2-hydroxyethyl)-4-methylbenzamide having a dehydration point prior to 120° C., and an X-ray powder diffraction pattern comprising peaks at 11.8±0.2, 15.8±0.2 and 26.9±0.2 degrees 2 theta.

Figure 2:
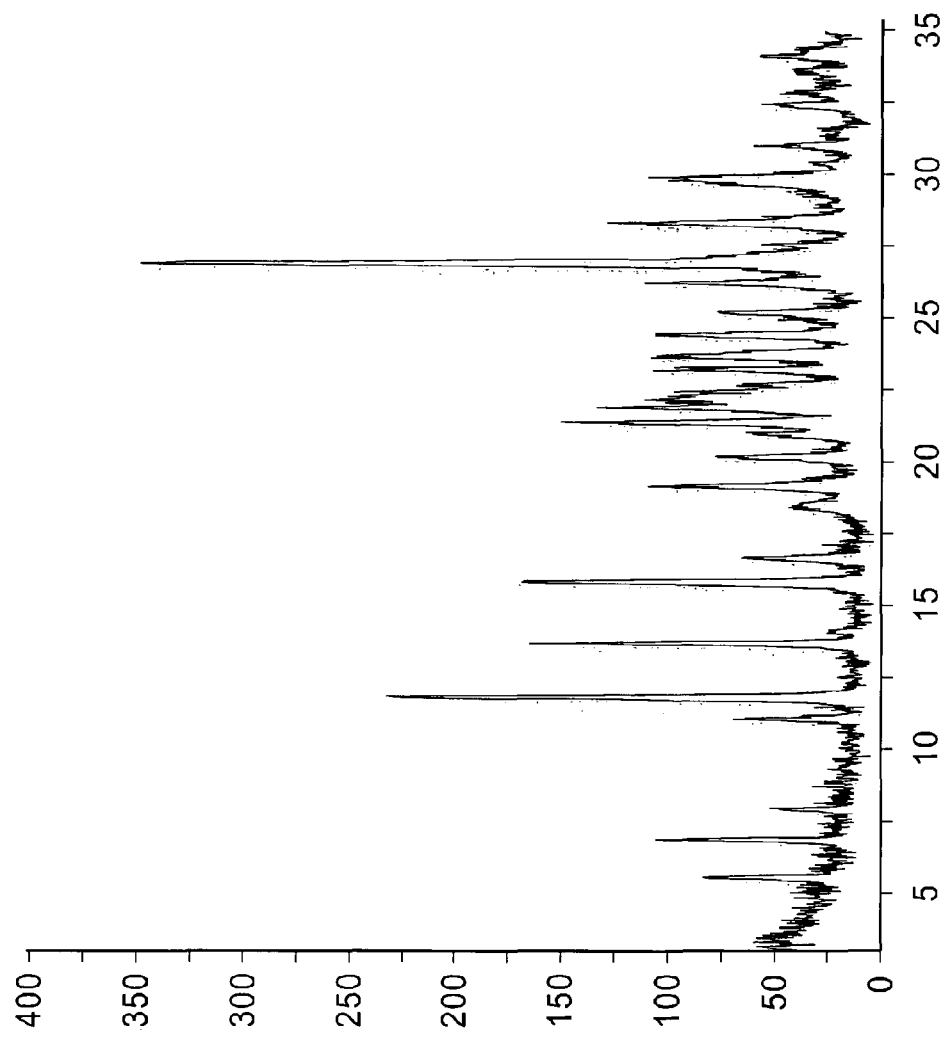
FIG. 2 shows an illustrative X-ray powder diffraction pattern for Form B.

FIG. 2 shows an illustrative X-ray powder diffraction pattern for Form B.

Table 3 presents data obtained for a sample of Form C.

TABLE 3

X-Ray Diffraction Data

| Angle (2-theta degrees) | d-value | Intensity (Counts) | Intensity (%) |
| --- | --- | --- | --- |
| 3.87 | 22.809 | 219 | 40.9 |
| 7.71 | 11.463 | 106 | 19.8 |
| 8.03 | 11.005 | 535 | 100 |
| 10.4 | 8.496 | 47 | 8.8 |
| 13.51 | 6.547 | 47 | 8.8 |
| 14.61 | 6.06 | 91 | 17 |
| 15.36 | 5.762 | 299 | 55.9 |
| 16.06 | 5.515 | 137 | 25.6 |
| 16.91 | 5.238 | 167 | 31.2 |
| 18.18 | 4.874 | 46 | 8.6 |
| 19.21 | 4.617 | 81 | 15.1 |
| 21.55 | 4.12 | 174 | 32.5 |
| 22.52 | 3.944 | 94 | 17.6 |
| 23.1 | 3.847 | 40 | 7.5 |
| 24.49 | 3.631 | 120 | 22.4 |
| 25.15 | 3.538 | 111 | 20.7 |
| 26.25 | 3.392 | 99 | 18.5 |
| 27.03 | 3.296 | 99 | 18.5 |
| 28.36 | 3.144 | 219 | 40.9 |
| 28.62 | 3.117 | 115 | 21.5 |
| 29.42 | 3.033 | 70 | 13.1 |
| 30.64 | 2.915 | 72 | 13.5 |
| 31.59 | 2.83 | 54 | 10.1 |

Figure 3:
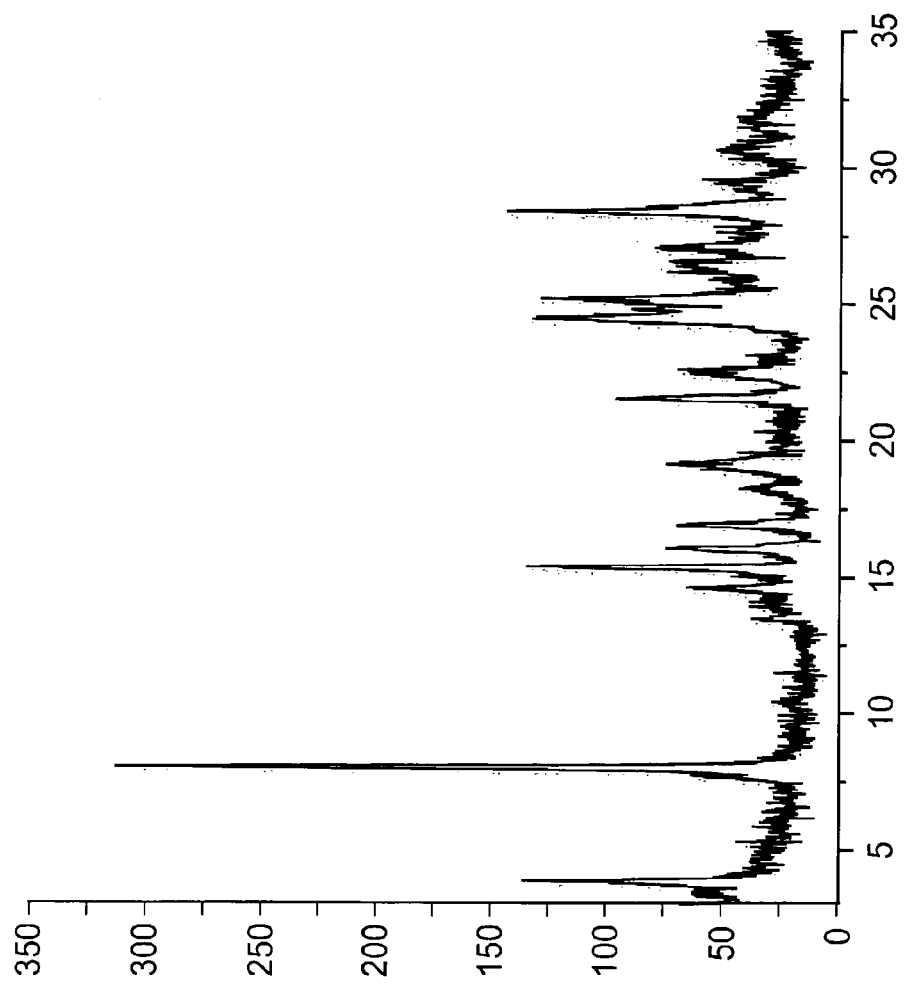
FIG. 3 shows an illustrative X-ray powder diffraction pattern for Form C.

FIG. 3 shows an illustrative X-ray powder diffraction pattern for Form C.

II. Differential Scanning Calorimetry (DSC)

A Mettler DSC822e heat flux differential scanning calorimeter (S/N 515) was used to collect the heat flow versus temperature data for the set of experiments. The samples were sealed in high-pressure gold-coated stainless steel (Au/SS) capsules for the experiments discussed in this report. A Julabo intercooler was used to maintain temperature control of this instrument. Dry nitrogen at 60 cc/min was used as the purge gas. Samples were heated at 3° C./min from 20° C. to 200° C. The Mettler Star software for Windows NT was used to collect the signal and analyze the data. The temperature and heat flow axis were calibrated using indium.

Figure 4:
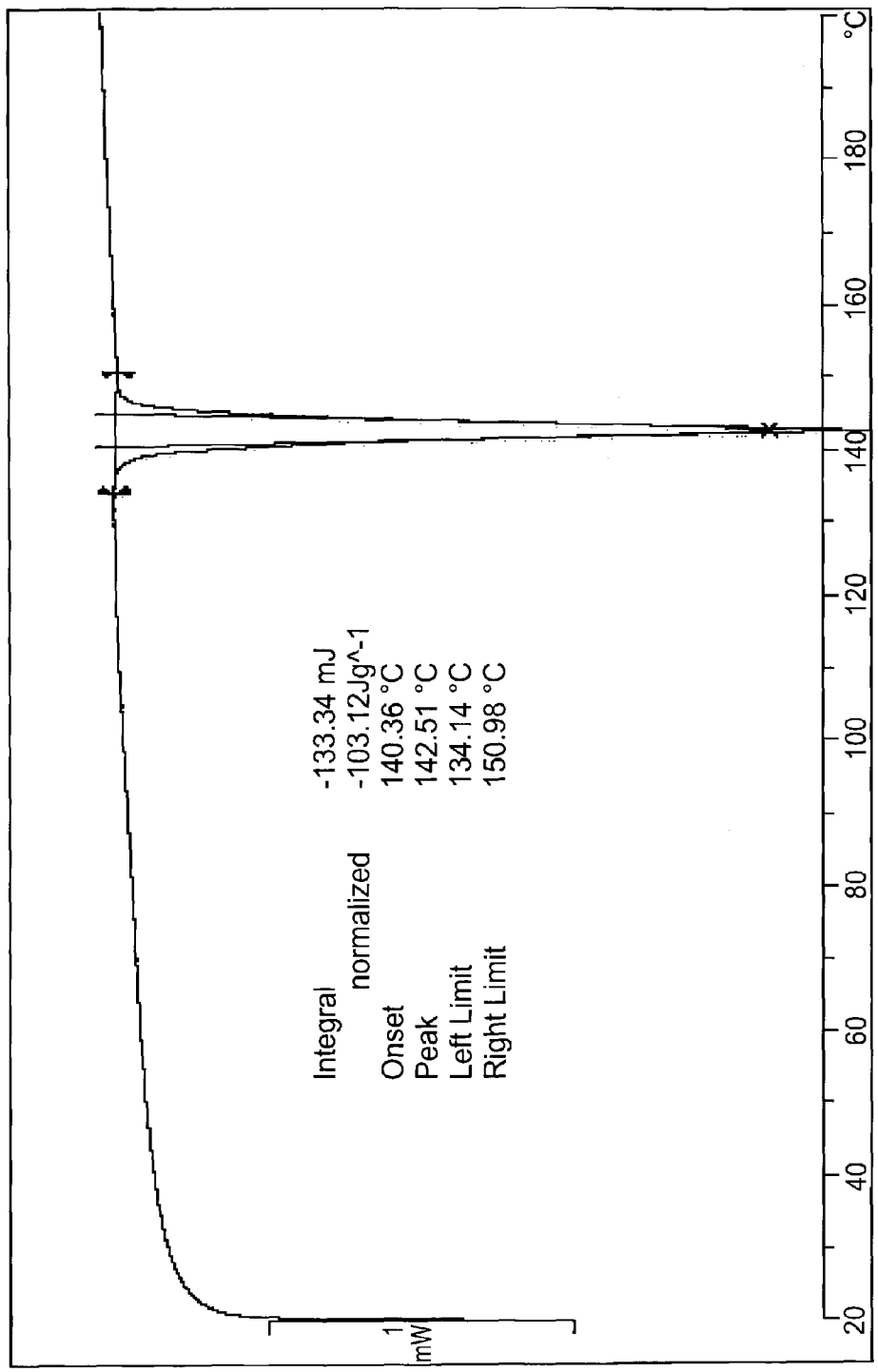
FIG. 4 shows an illustrative differential scanning calorimetry thermogram of Form A.

FIG. 4 shows an illustrative differential scanning calorimetry thermogram of Form A.

Figure 5:
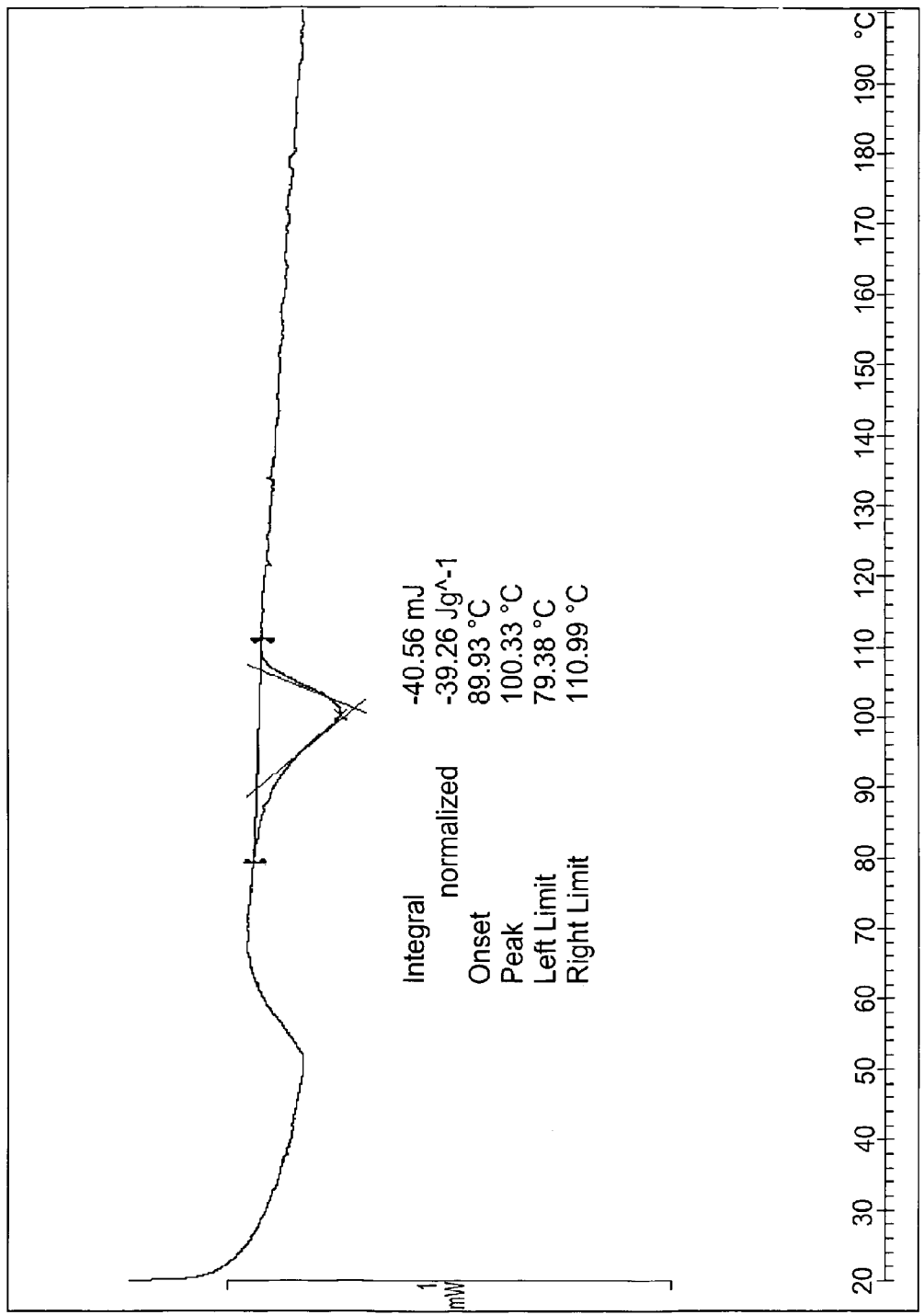
FIG. 5 shows an illustrative differential scanning calorimetry thermogram of Form C.

FIG. 5 shows an illustrative differential scanning calorimetry thermogram of Form C.

DSC can also be used to characterize Form B.

III. Thermogravimetric Analysis/Simultaneous Differential Thermal Analysis (TGA/SDTA)

A Mettler TGA/SDTA851e thermogravimetric analyzer simultaneous differential thermal analyzer (S/N 286) was used to collect the weight loss and sample temperature versus temperature data. The samples were sealed in 40 uL pierceable aluminum capsules. The instrument robot was used to pierce the samples before insertion into the furnace. A Julabo circulator was used to maintain temperature control of this instrument. Dry nitrogen at 50 cc/min was used as the purge gas. Samples were heated at 5° C./min from 20° C. to 400° C. The Mettler Star software for Windows NT was used to collect the signal and analyze the data. The temperature and simulated heat flow axis were calibrated using indium.

Figure 6:
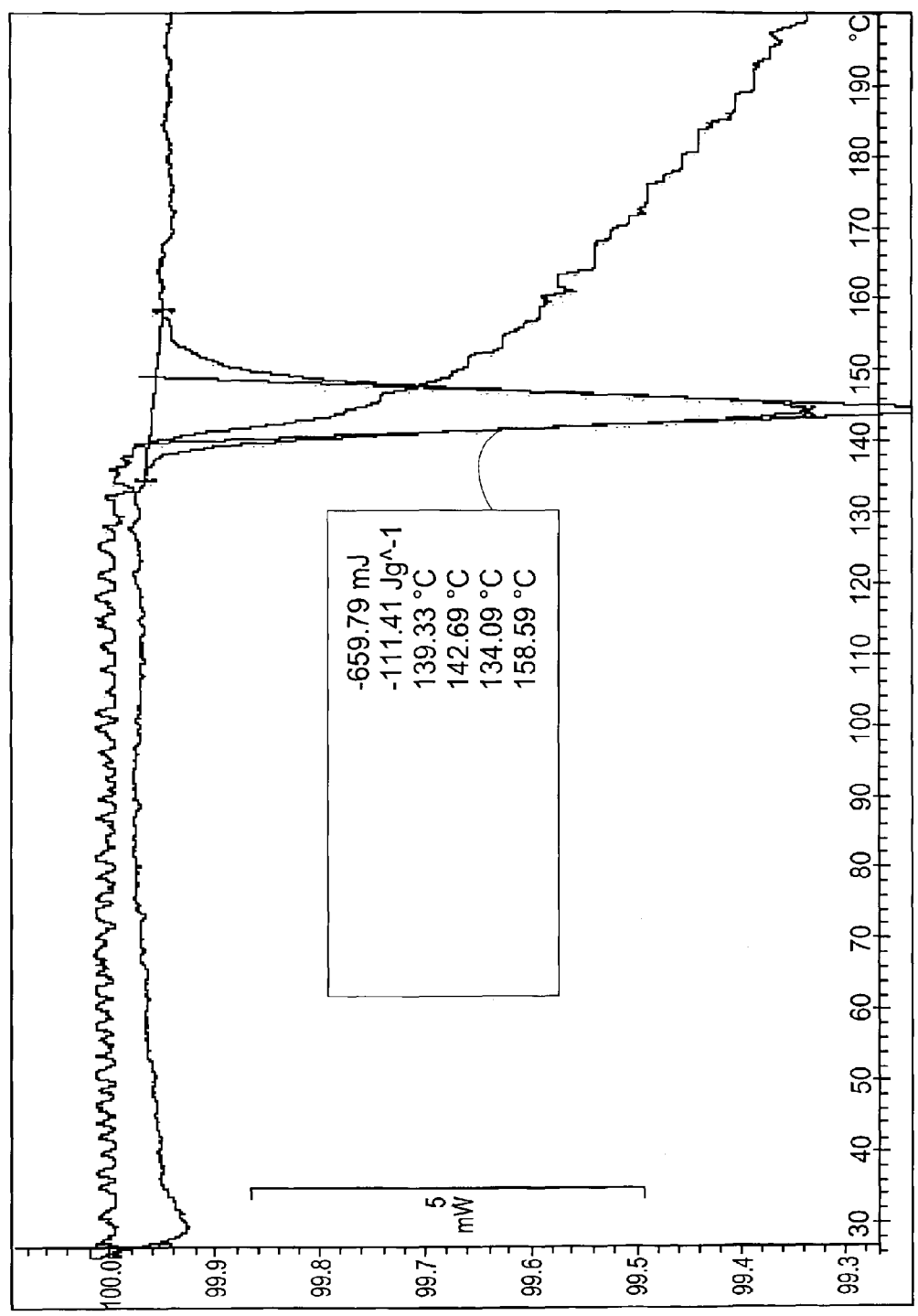
FIG. 6 shows an illustrative Thermogravimetric Analysis of Form A.

FIG. 6 shows an illustrative Thermogravimetric Analysis of Form A.

Figure 7:
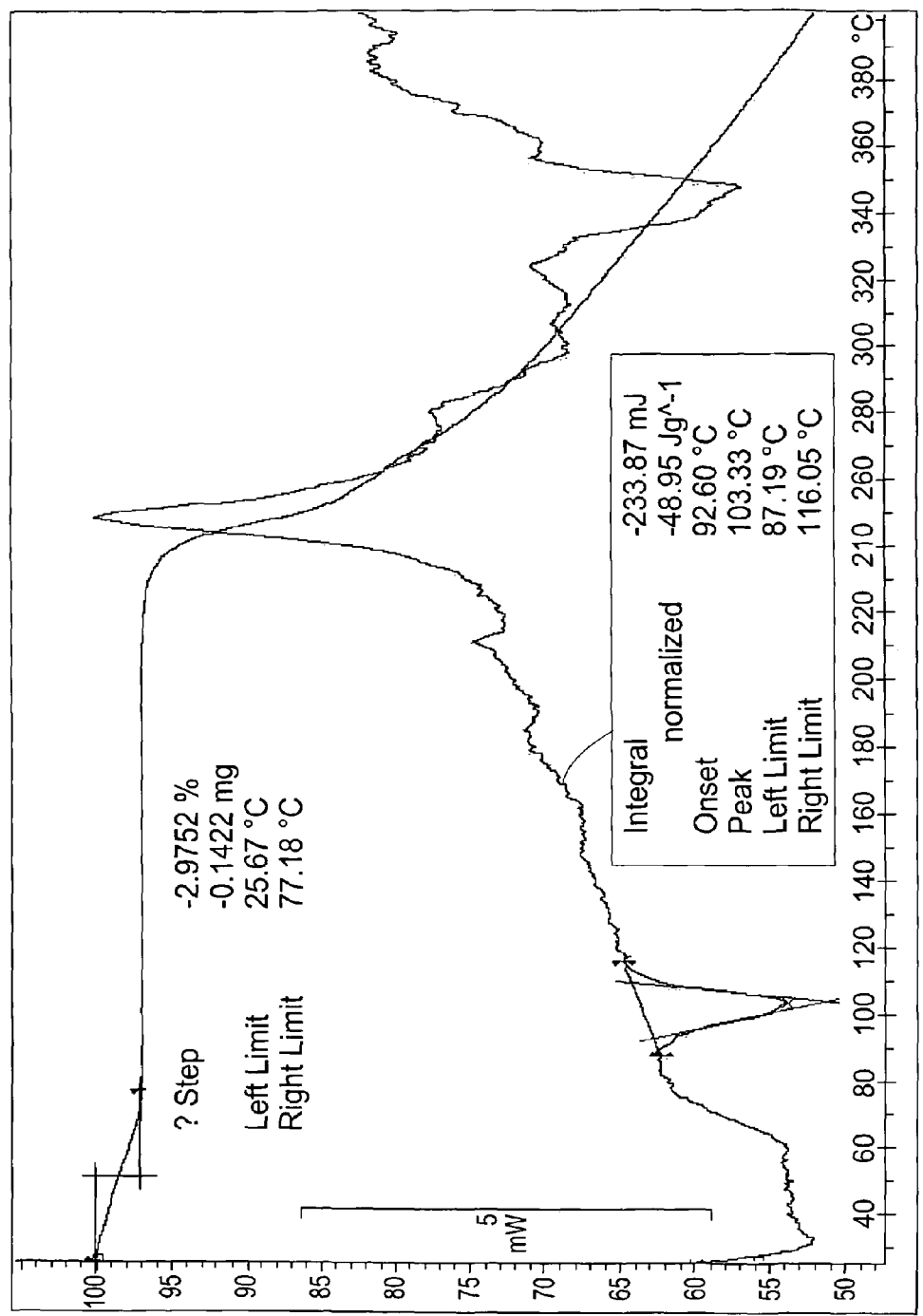
FIG. 7 shows an illustrative Thermogravimetric Analysis of Form C.

FIG. 7 shows an illustrative Thermogravimetric Analysis of Form C.

Thermogravimetric Analysis can also be used to characterize Form B.

IV. Infrared Spectroscopy

Infrared Spectroscopy was done on a Thermo-Nicolet Corporation Nexus 670 FT-IR using an Avatar Ge ATR Omni-Sampler. Up to 64 scans with a 4 cm$^{-1}$ resolution were averaged to reduce noise. A KBr beamsplitter and a MCT/A detector were employed.

Table 4 presents data obtained for a sample of Form A.

TABLE 4

| Position | Intensity |
|---|---|
| 1070.37 | 0.196 |
| 773.03 | 0.153 |
| 1503.92 | 0.146 |
| 1640.83 | 0.14 |
| 1655.18 | 0.137 |
| 960.15 | 0.122 |
| 805.24 | 0.117 |
| 1330.79 | 0.109 |
| 1311.43 | 0.108 |
| 1462.76 | 0.105 |
| 1094.36 | 0.103 |
| 1514.67 | 0.102 |
| 870.28 | 0.0998 |
| 1276.64 | 0.0939 |
| 1593.56 | 0.0913 |
| 1545.85 | 0.083 |
| 969.8 | 0.0828 |
| 1139 | 0.0803 |
| 1221.84 | 0.0777 |
| 1418.17 | 0.0777 |
| 723.97 | 0.0751 |
| 750.18 | 0.0685 |
| 1568.53 | 0.0631 |
| 1384.13 | 0.0503 |
| 1199.82 | 0.0456 |

TABLE 4-continued

| Position | Intensity |
|---|---|
| 1251.67 | 0.041 |
| 924.16 | 0.0391 |
| 691.81 | 0.0385 |
| 3362.38 | 0.0344 |
| 712.22 | 0.0294 |
| 846.67 | 0.0289 |

Table 5 presents data obtained for a sample of Form B.

TABLE 5

| Position | Intensity |
|---|---|
| 1661.08 | 0.117 |
| 1079.48 | 0.0586 |
| 1331.71 | 0.0551 |
| 1068.84 | 0.0496 |
| 1439.27 | 0.0434 |
| 1641.82 | 0.0409 |
| 1426.43 | 0.0328 |
| 1509.71 | 0.0299 |
| 1246.63 | 0.0294 |
| 1549.33 | 0.0286 |
| 1268.15. | 0.0254 |
| 1596.06 | 0.0213 |
| 1558.33 | 0.0186 |
| 1457.12 | 0.0178 |
| 1373.24 | 0.0161 |
| 962.65 | 0.0134 |
| 1092.33 | 0.0125 |
| 1618.08 | 0.0104 |
| 1575.82 | 0.0079 |
| 3346.22 | 0.0062 |
| 1683.99 | 0.0053 |
| 887.48 | 0.0045 |
| 1142.82 | 0.0023 |
| 1384 | 0.0019 |
| 3653.34 | 0.0014 |
| 1700.49 | 0.0011 |
| 3048.87 | −0.0046 |
| 1185.05 | −0.0046 |
| 1044.46 | −0.0064 |
| 926.78 | −0.008 |
| 1718.15 | −0.0097 |

Figure 8:
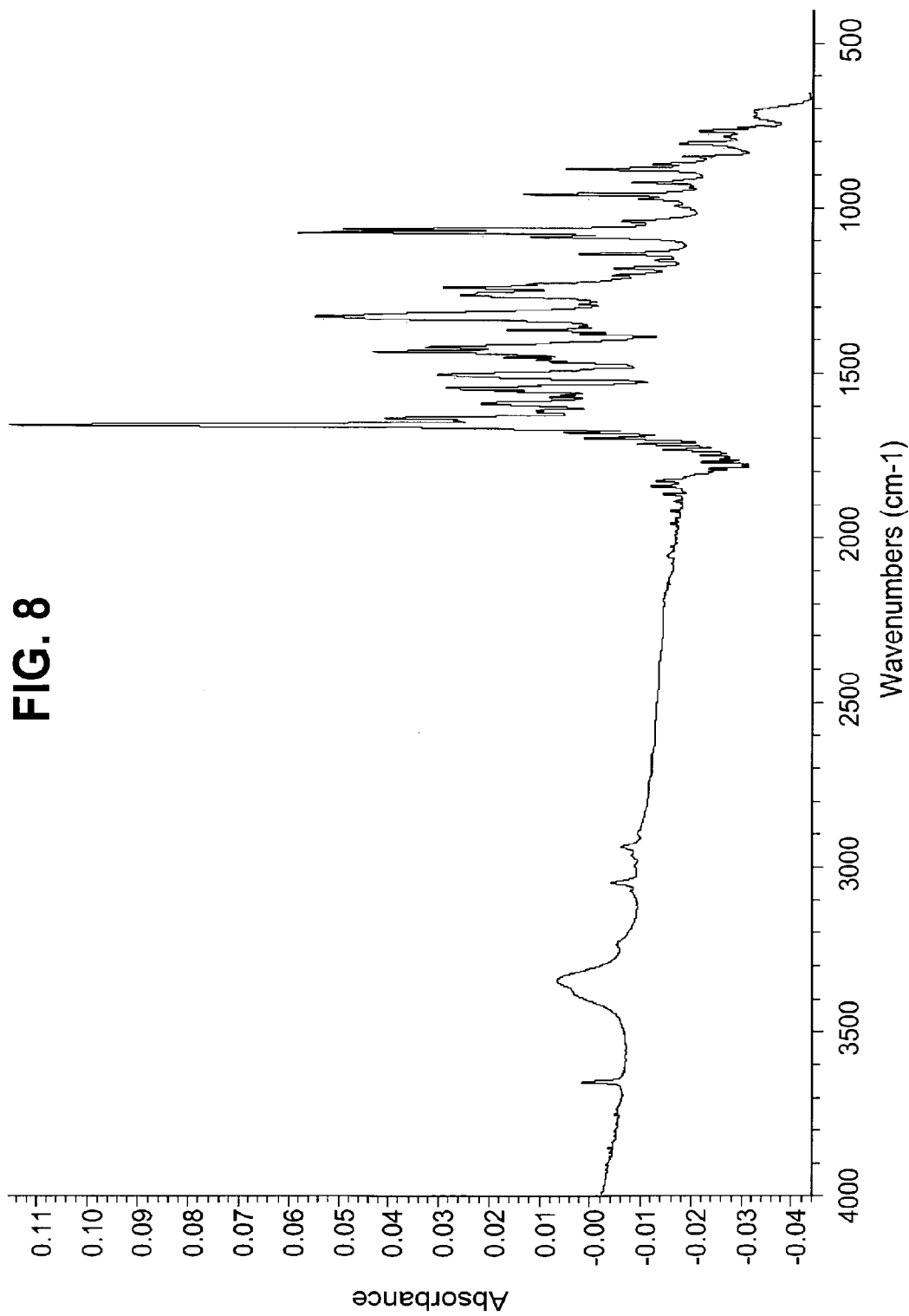
FIG. 8 shows an illustrative infrared (IR) spectrum of Form B.

FIG. 8 shows an illustrative infrared (IR) spectrum of Form B.

V. Raman Spectroscopy

Raman spectra were obtained on a FT-Raman module with a FT-Raman micro view stage. The FT-Raman module was attached to the Nexus 670 Bench. A CaF$_2$ beamsplitter and a Ge detector were used. Up to 128 scans with a resolution of 2 cm$^{-1}$ were done on each sample. Both instruments were controlled by Omnic 6.0A software. Atlus mapping 6.0 software was used to control the Raman view stage.

Table 6 presents data obtained for a sample of Form A.

TABLE 6

| Position | Intensity |
|---|---|
| 1616.87 | 5.411 |
| 3076.75 | 5.193 |
| 1515.08 | 5.004 |
| 832.65 | 4.815 |
| 1310.32 | 3.871 |
| 1331.95 | 3.596 |
| 661.95 | 3.363 |
| 1301.64 | 3.187 |
| 2927.48 | 3.116 |
| 1273.48 | 3.1 |
| 1251.69 | 2.994 |

TABLE 6-continued

| Position | Intensity |
|---|---|
| 725.58 | 2.829 |
| 1638.1 | 2.756 |
| 2966.89 | 2.552 |
| 1455.18 | 2.457 |
| 1284.12 | 2.366 |
| 1417.57 | 2.35 |
| 785.78 | 2.338 |
| 1426.06 | 2.223 |
| 581.69 | 2.23 |
| 1666.31 | 2.073 |
| 1549.95 | 1.998 |
| 969.66 | 1.982 |
| 926.48 | 1.916 |
| 751.68 | 1.728 |
| 891.22 | 1.672 |
| 2998.34 | 1.649 |
| 2905.82 | 1.581 |
| 493.36 | 1.585 |
| 1376.98 | 1.504 |
| 1463.55 | 1.465 |
| 1568.51 | 1.391 |
| 1051.15 | 1.38 |
| 1385.12 | 1.364 |
| 1095 | 1.313 |
| 455.15 | 1.286 |
| 525.74 | 1.183 |
| 874.33 | 1.184 |
| 847.24 | 1.145 |
| 2864.24 | 1.047 |
| 749.02 | 1.021 |
| 2856.67 | 1.01 |
| 1228.21 | 0.956 |
| 959.63 | 0.949 |
| 607.84 | 0.933 |
| 763.61 | 0.921 |

Table 7 presents data obtained for a sample of Form B.

TABLE 7

| Position | Intensity |
|---|---|
| 1621.36 | 12.21 |
| 1329.64 | 8.292 |
| 1271.06 | 7.127 |
| 845.6 | 6.976 |
| 2930.54 | 6.653 |
| 1514.53 | 6.52 |
| 730.17 | 6.452 |
| 243.72 | 4.6 |
| 1665 | 4.088 |
| 335.71 | 4.041 |
| 3083.93 | 3.886 |
| 112.52 | 3.863 |
| 1419.75 | 3.709 |
| 157.14 | 3.505 |
| 1646.24 | 3.466 |
| 3050.99 | 3.398 |
| 891.3 | 3.338 |
| 1436.11 | 3.31 |
| 1247.4 | 3.287 |
| 592.4 | 3.169 |
| 223.76 | 2.857 |
| 1555.17 | 2.767 |
| 1234.46 | 2.387 |
| 2898.85 | 2.383 |
| 870.16 | 2.174 |
| 360.9 | 2.162 |
| 575 | 2.148 |
| 276.76 | 2.121 |
| 1092.56 | 2.09 |
| 1459.18 | 2.011 |
| 512.63 | 1.994 |
| 675.27 | 1.98 |
| 1044.27 | 1.823 |
| 764.63 | 1.748 |

TABLE 7-continued

| Position | Intensity |
|---|---|
| 1081.74 | 1.712 |
| 1383.55 | 1.625 |
| 973.92 | 1.565 |
| 1364.05 | 1.545 |
| 1140.52 | 1.532 |
| 2995.19 | 1.526 |
| 460.82 | 1.437 |
| 917.05 | 1.336 |
| 962.85 | 1.321 |
| 1067.31 | 1.272 |
| 491.9 | 1.243 |
| 815.25 | 1.234 |
| 1205.8 | 1.124 |
| 633.97 | 0.863 |

Figure 9:
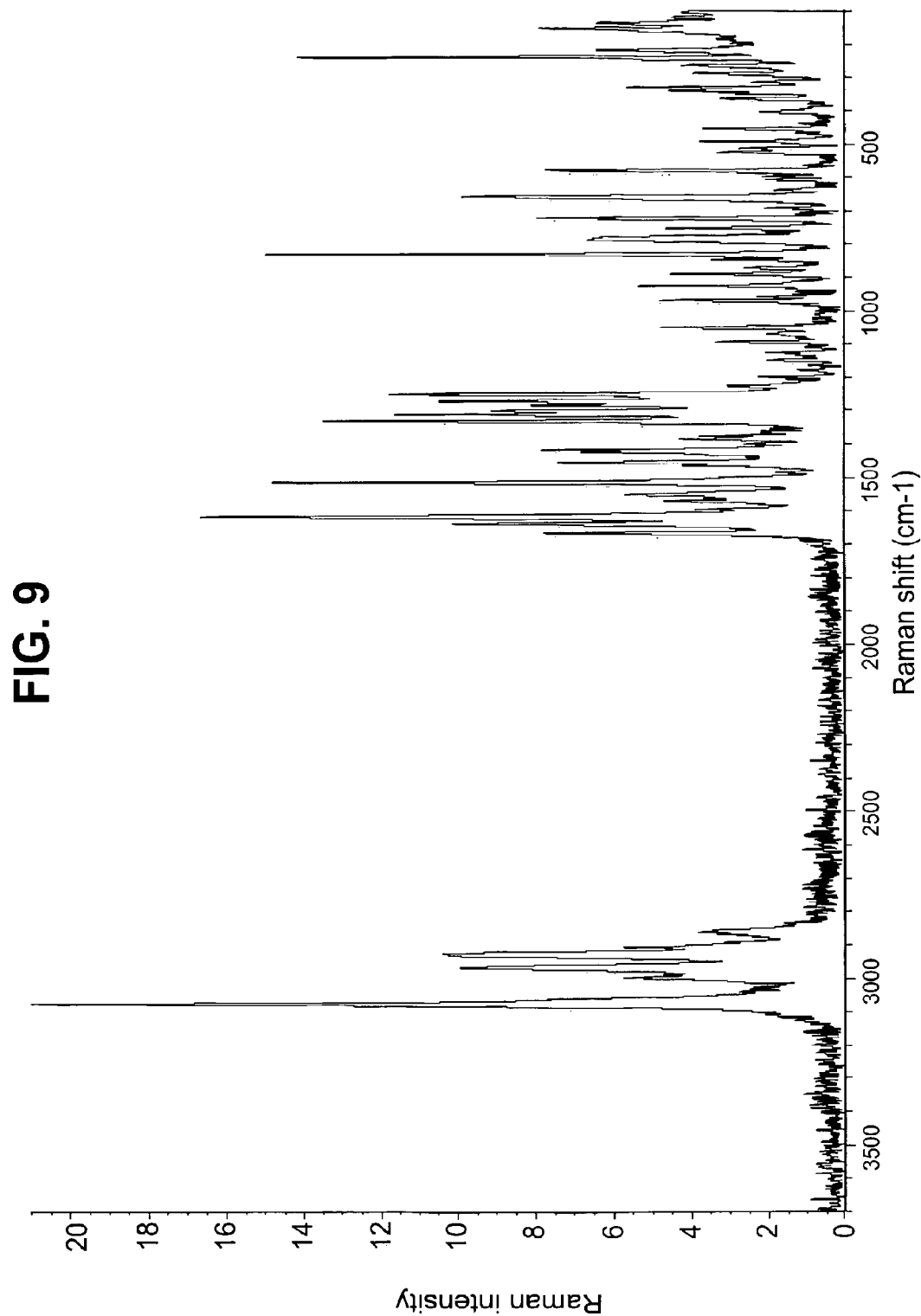
FIG. 9 shows an illustrative Raman spectrum of Form A.

FIG. 9 shows an illustrative Raman spectrum of Form A.

Figure 10:
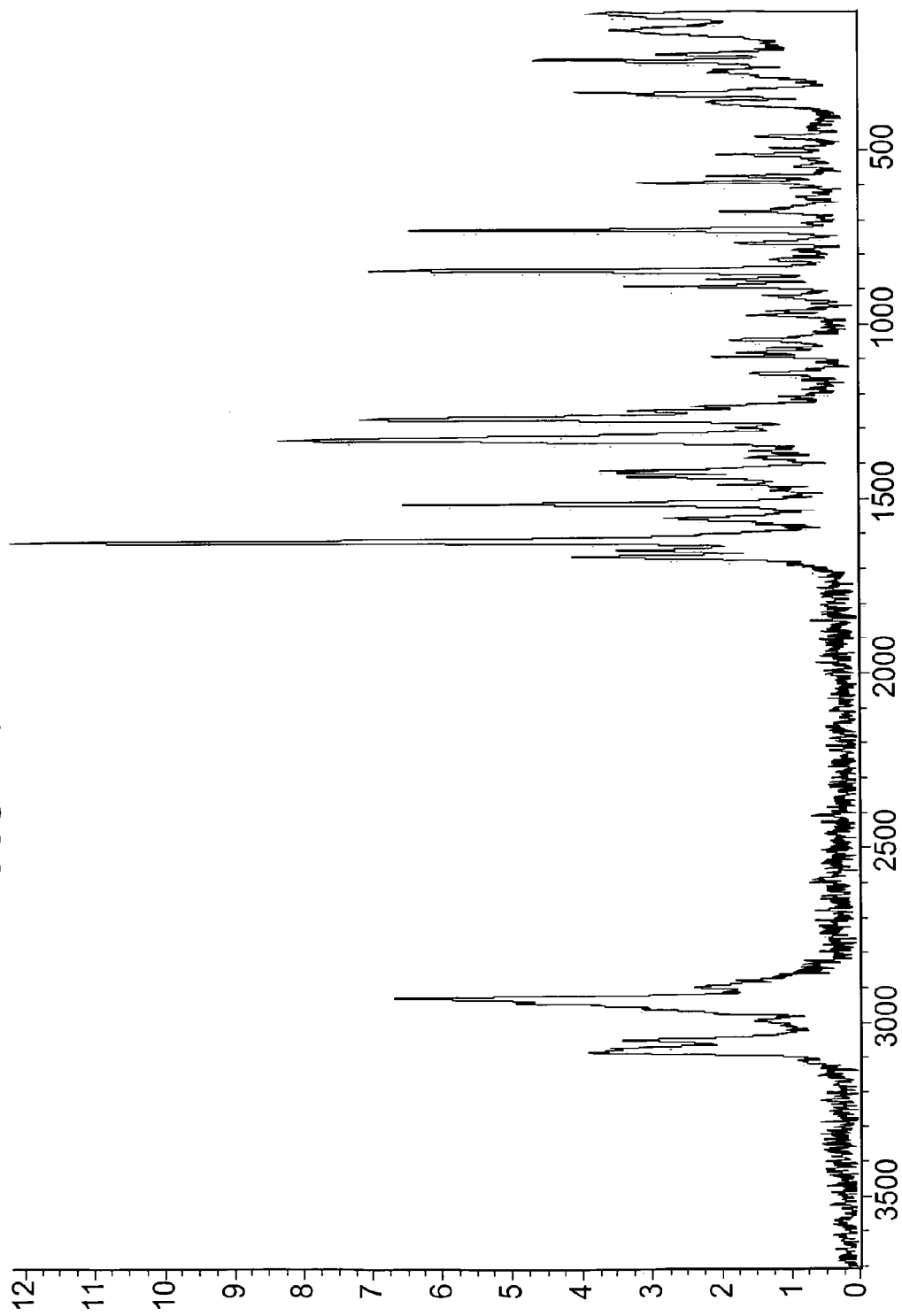
FIG. 10 shows an illustrative Raman spectrum of Form B.

FIG. 10 shows an illustrative Raman spectrum of Form B.

VI. Dynamic Vapor Sorption (DVS)

DVS was carried out on a Surface Measurement Systems DVS 1 (S/N 990909, Balance #81317) operating under DVS Win version 2.18 and Windows 2000 software. The system was previously calibrated using known relative humidity generated by saturated salt solutions at 11.8%, 33.1% and 75% relative humidity (RH). Two scans were done at 25° C. from 0-90-0% RH with a step size of 10% RH and a dm/dt of 0.005. Quartz sample pans were used for all analyses.

Figure 11:
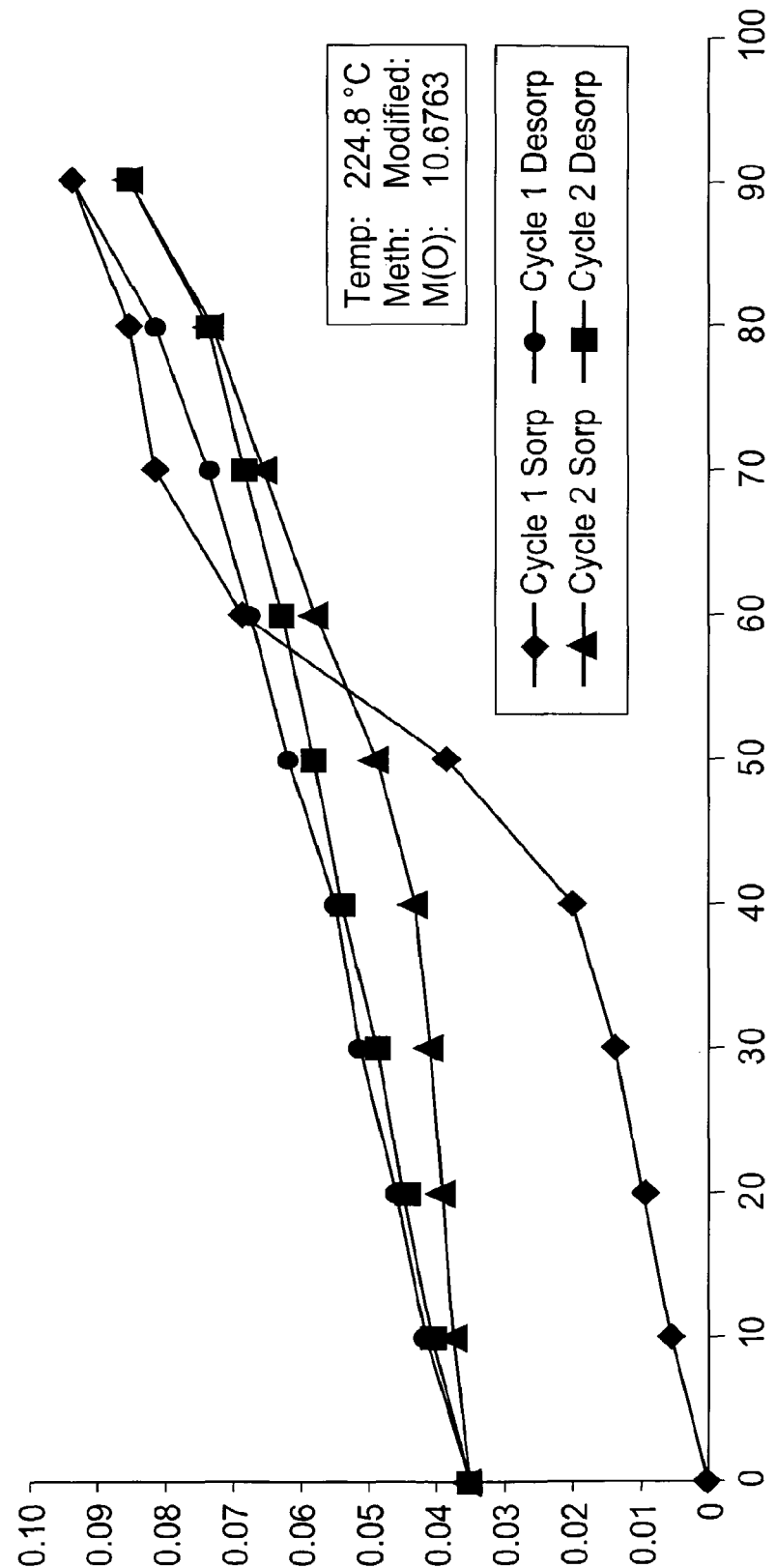
FIG. 11 shows an illustrative DVS of Form A.

FIG. 11 shows an illustrative DVS of Form A.

Figure 12:
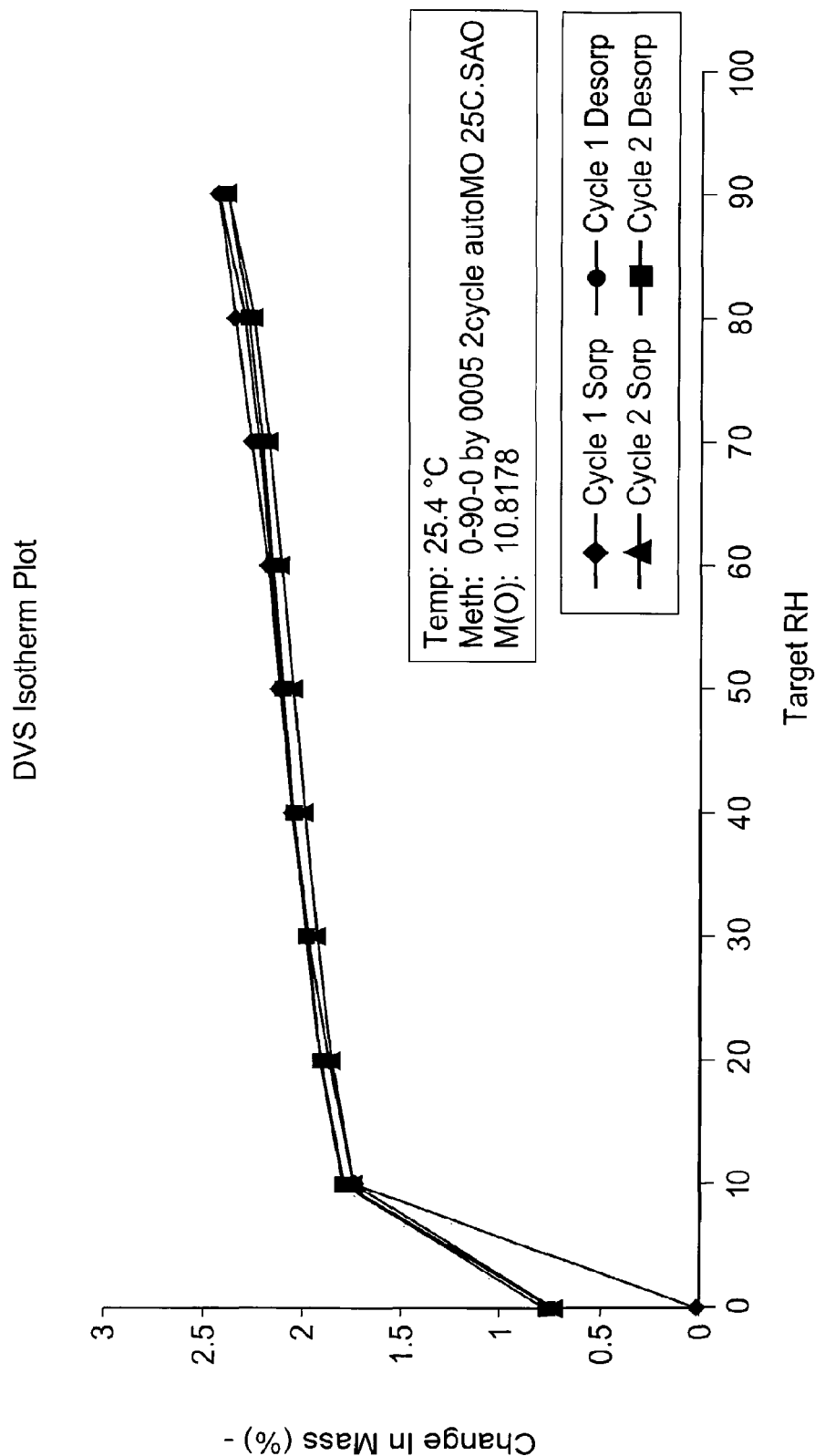
FIG. 12 shows an illustrative DVS of Form B.

FIG. 12 shows an illustrative DVS of Form B.

Figure 13:
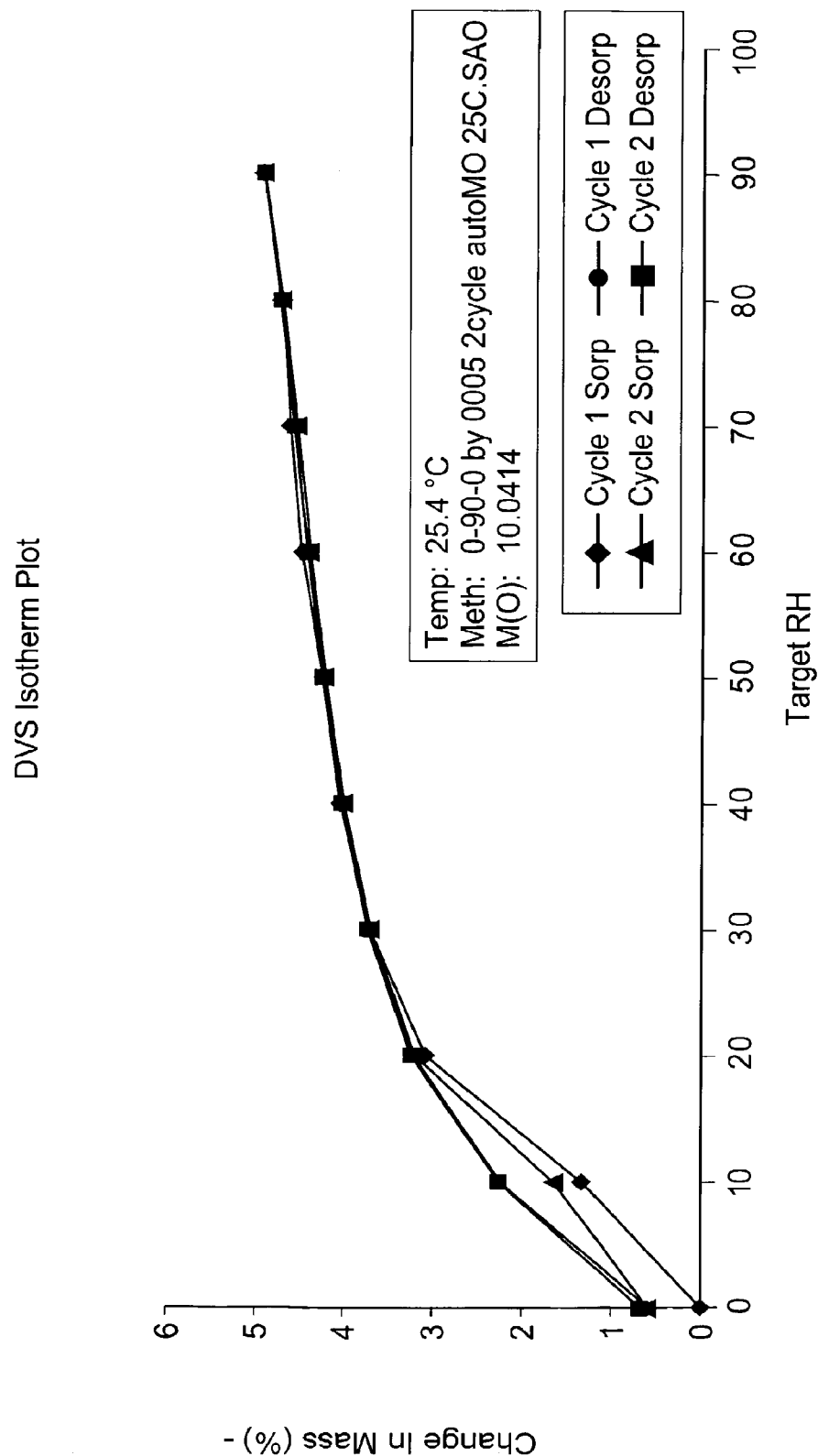
FIG. 13 shows an illustrative DVS of Form C.

FIG. 13 shows an illustrative DVS of Form C.

Pharmaceutical Compositions

The present invention is further directed to pharmaceutical compositions comprising the crystalline form of Compound 1.

In one embodiment, the pharmaceutical composition comprises Form A and (ii) one or more pharmaceutically acceptable carriers and/or diluents and/or adjuvants (collectively referred to herein as "excipients") and, optionally, (iii) one or more active ingredients other than Compound 1.

In another embodiment, essentially the entire amount of Compound 1 contained in the composition is present as substantially phase pure Form A.

In one embodiment, at least a detectable fraction of Compound 1 is present in the form of Form A.

In another embodiment, at least fifty percent (50%) of Compound 1 is present in the form of Form A.

In another embodiment, at least ninety percent (90%) of Compound 1 is present in the form of Form A.

In yet another embodiment, a pharmaceutical composition comprising 3-[5-chloro-4-[(2,4-difluorobenzyl)oxy]-6-oxopyrimidin-1(6H)-yl]-N-(2-hydroxyethyl)-4-methylbenzamide and one or more pharmaceutically acceptable excipients, wherein a detectable amount of the 3-[5-chloro-4-[(2,4-difluorobenzyl)oxy]-6-oxopyrimidin-1(6H)-yl]-N-(2-hydroxyethyl)-4-methylbenzamide is present as Form A crystalline 3-[5-chloro-4-[(2,4-difluorobenzyl)oxy]-6-oxopyrimidin-1(6H)-yl]-N-(2-hydroxyeth yl)-4-methylbenzamide, wherein Form A has a melting point in a range from about 138.5° C. to about 142.5° C., and an X-ray powder diffraction pattern comprising peaks at 13.5±0.2, 21.1±0.2 and 27.2±0.2 degrees 2 theta.

In one embodiment, the pharmaceutical composition comprises Form B and (ii) one or more pharmaceutically acceptable carriers and/or diluents and/or adjuvants (collectively referred to herein as "excipients") and, optionally, (iii) one or more active ingredients other than Compound 1.

In another embodiment, essentially the entire amount of Compound 1 contained in the composition is present as substantially phase pure Form B.

In one embodiment, at least a detectable fraction of Compound 1 is present in the form of Form B.

In another embodiment, at least fifty percent (50%) of Compound 1 is present in the form of Form B.

In another embodiment, at least ninety percent (90%) of Compound 1 is present in the form of Form B.

In yet another embodiment, a pharmaceutical composition comprising 3-[5-chloro-4-[(2,4-difluorobenzyl)oxy]-6-oxopyrimidin-1(6H)-yl]-N-(2-hydroxyethyl)-4-methylbenzamide and one or more pharmaceutically acceptable excipients, wherein a detectable amount of the 3-[5-chloro-4-[(2,4-difluorobenzyl)oxy]-6-oxopyrimidin-1(6H)-yl]-N-(2-hydroxyethyl)-4-methylbenzamide is present as Form B crystalline 3-[5-chloro-4-[(2,4-difluorobenzyl)oxy]-6-oxopyrimidin-1(6H)-yl]-N-(2-hydroxyethyl)-4-methylbenzamide, wherein Form B has a dehydration point prior to 120° C., and an X-ray powder diffraction pattern comprising peaks at 11.8±0.2, 15.8±0.2 and 26.9±0.2 degrees 2 theta.

The compound of the present invention can be administered to the subject as the neat compound alone. Alternatively the compounds of the present invention can be presented with one or more pharmaceutically acceptable excipients in the form of a pharmaceutical composition. A useful excipient can be, for example, a carrier. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present, including other compounds of the present invention. The pharmaceutical compositions of the invention can be prepared by any of the well known techniques of pharmacy, consisting essentially of admixing the components.

These compounds can be administered by any conventional means available for use in conjunction with pharmaceuticals, either as individual therapeutic compounds or as a combination of therapeutic compounds.

The amount of compound which is required to achieve the desired biological effect will, of course, depend on a number of factors such as the specific compound chosen, the use for which it is intended, the mode of administration, and the clinical condition of the recipient.

The compositions of the invention generally can be presented in a dosage form containing about 0.1 mg to about 1000 mg of the crystalline form of Compound 1. In other embodiments, the dosage form contains about 0.1 mg to about 500 mg, 0.2 mg to about 600 mg, about 0.3 mg to about 250 mg, about 0.4 mg to about 150 mg, about 0.5 mg to about 100 mg, about 1 mg to about 100 mg, about 0.6 mg to about 50 mg, about 0.7 mg to about 25 mg, about 0.8 mg to about 15 mg, about 0.9 mg to about 10 mg, or about 1 mg to about 5 mg of the crystalline form of Compound 1. In still other embodiments, the dosage form contains less than about 100 mg, less than about 75 mg, less than about 50 mg, less than about 25 mg, or less than about 10 mg of the crystalline form of Compound 1. This total daily dose can be administered to the patient in a single dose, or in proportionate multiple subdoses. Subdoses can be administered 2 to 6 times per day. Doses can be in sustained release form effective to obtain desired results.

Illustrative non-limiting dosage unit forms of the pharmaceutical compositions can typically contain, for example, 0.1, 0.2, 0.5, 1, 2, 3, 4, 5, 6, 7, 8, 9 10, 20, 25, 30, 37.5, 40, 50, 75, 100, 125, 150, 175, 200, 250, 300, 350 or 400 mg of the crystalline form of Compound 1.

Oral delivery of the compound of the present invention can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

When administered intravenously, the daily dose can, for example, be in the range of from about 0.1 mg/kg body weight to about 20 mg/kg body weight, preferably from about 0.25 mg/kg body weight to about 10 mg/kg body weight, more preferably from about 0.4 mg/kg body weight to about 5 mg/kg body weight. This dose can be conveniently administered as an infusion of from about 10 ng/kg body weight to about 2000 ng/kg body weight per minute. Infusion fluids suitable for this purpose can contain, for example, from about 0.1 ng to about 10 mg, preferably from about 1 ng to about 200 mg per milliliter. Unit doses can contain, for example, from about 1 mg to about 200 g of the compound of the present invention. Thus, ampoules for injection can contain, for example, from about 1 mg to about 200 mg.

Pharmaceutical compositions according to the present invention include those suitable for oral, rectal, topical, buccal (e.g., sublingual), and parenteral (e.g., subcutaneous, intramuscular, intradermal, or intravenous) administration, although the most suitable route in any given case will depend on the nature and severity of the condition being treated and on the nature of the particular compound which is being used. In most cases, the preferred route of administration is oral.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w.

Pharmaceutical compositions suitable for oral administration can be presented in discrete units, such as capsules, cachets, lozenges, or tablets, each containing a predetermined amount of at least one compound of the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or molding a powder or granules of the compound, optionally with one or more assessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be made by molding, in a suitable machine, the powdered compound moistened with an inert liquid diluent.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of the present invention. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of a compound disclosed herein.

Pharmaceutical compositions suitable for rectal administration are preferably presented as unit-dose suppositories. These can be prepared by admixing a compound of the present invention with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include vaseline, lanoline, polyethylene glycols, alcohols, and combinations of two or more thereof. The active compound is generally present at a concentration of from 0.1 to 15% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain a compound of the present invention in an optionally buffered, aqueous solution, dissolved and/or dispersed in an adhesive, or dispersed in a polymer. A suitable concentration of the active compound is about 1% to 35%, preferably about 3% to 15%. As one particular possibility, the compound can be delivered from the patch by electrotransport or iontophoresis, for example, as described in Pharmaceutical Research, 3(6), 318 (1986).

In any case, the amount of active ingredient that can be combined with carrier materials to produce a single dosage form to be administered will vary depending upon the host treated and the particular mode of administration.

The solid dosage forms for oral administration including capsules, tablets, pills, powders, and granules noted above comprise one or more compounds of the present invention admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleaginous suspensions may be formulated according to the known art using suitable dispersing or setting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutically acceptable carriers encompass all the foregoing and the like.

Methods of Treatment and/or Prophylaxis

The present invention also embraces a method for treatment and/or prophylaxis of a p38 kinase-mediated condition, the method comprising treating a subject having or susceptible to such condition or disorder with a therapeutically effective amount of a solid-state form of Compound 1 or a pharmaceutical composition containing a solid-state form of Compound 1.

In one embodiment the p38 kinase-mediated condition is rheumatoid arthritis.

Such a method is useful for treatment and/or prophylaxis of a condition in a subject where administration of a p38 kinase inhibitor is indicated, including, but not limited to, treatment of those conditions previously disclosed above.

Besides being useful for human treatment, the solid-state forms of Compound 1 and pharmaceutical compositions thereof are also useful for veterinary treatment of companion, exotic and farm animals, for example horses, dogs, and cats.

The solid-state forms of Compound 1 and compositions thereof also can be used (i) in therapies partially or completely in place of other anti-inflammatory drugs, and/or (ii) in combination therapies with other drugs. Such anti-inflammatory and other drugs may include, but are not limited to, steroids, cyclooxygenase-2 inhibitors, DMARD's, immunosuppressive agents, NSAIDs, 5-lipoxygenase inhibitors, $LTB_4$ antagonists and $LTA_4$ hydrolase inhibitors. The phrase "combination therapy" embraces administration of each drug in a sequential manner in a regimen that will provide beneficial effects of the drug combination, as well as co-administration of the drugs in a substantially simultaneous manner, such as in a single capsule or injection having a fixed ratio of these active agents or in multiple, separate dosage forms or injections, one for each agent.

EXAMPLES

The following contain detailed descriptions of methods of preparation of the crystalline forms of Compound 1 described herein. This detailed descriptions fall within the scope of the invention and illustrate the invention without in any way restricting that scope. All percentages are by weight unless otherwise indicated.

Example 1

Preparation of amorphous 3-[(5-chloro-4-[(2,4-difluorobenzyl)oxy]-6-oxopyrimidin-1(6H)-yl]-N-(2-hydroxyethyl)-4-methylbenzamide

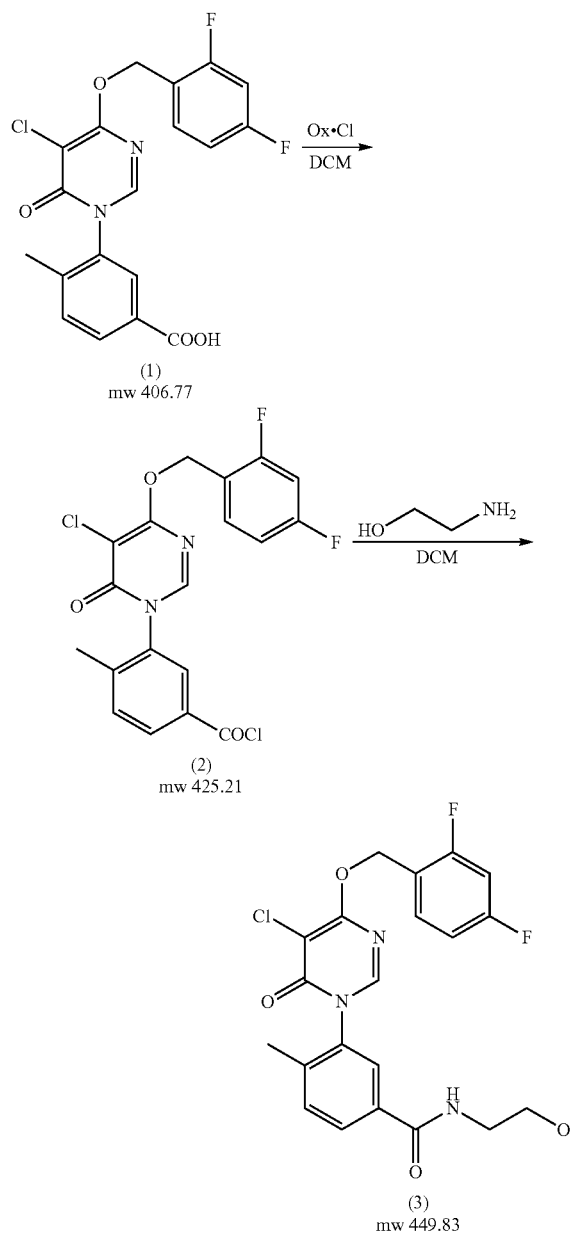

A suspension of (1) (30.0 g, 73.75 mmol) in dichloromethane (300 mL) was treated with 9 drops of DMF followed by oxalyl chloride (14.04 g, 9.63 mL, 110.6 mmol, 1.5 eq). The mixture was stirred at room temperature for 18 hours. A clear solution was formed. The solution was concentrated on a rotavap to give an off-white solid. The solid was treated again with approx. 300 mL of dichloromethane (the solid was not completely soluble) and added to an ice-cold solution of ethanolamine (21.0 g, 360 mmol) in dichloromethane (300 mL) in one portion. The mixture was then stirred at room temperature for 30 min. LC indicated complete reaction (2). The reaction mixture was then washed with 3N HCl (300 mL). The layers separated. The organic layer was washed with water (300 mL), Once again layers separated. Addition of iso-propanol was used to clarify the organic layer. Approx. 75 mL of iso-propanol was added and the organic layer was washed with 1M potassium carbonate and dried over anhydrous sodium sulfate. The solvent was evaporated and the residue was flash chromatographed over 350 g of silica gel and eluted with dichloromethane (1.0 lit) followed by 10% methanol in dichloromethane (2 lit). Fractions containing the desired product were combined, concentrated and dried under vacuum to give the product as a white amorphous solid (31.76 g, 95.7%).

Example 2

Preparation of Form A

Form A was prepared by dissolving 34 mg of amorphous 3-[5-chloro-4-[(2,4-difluorobenzyl)oxy]-6-oxopyrimidin-1 (6H)-yl]-N-(2-hydroxyethyl)-4-methylbenzamide in 0.5 ml of methyl ethyl ketone. The mixture was allowed to air dry in a hood resulting in Form A.

Form A can also be prepared by the recrystallization from methyl t-butyl ether. 35 mg amorphous 3-[5-chloro-4-[(2,4-difluorobenzyl)oxy]-6-oxopyrimidin-1(6H)-yl]-N-(2-hydroxyethyl)-4-methylbenzamide is dissolved in 0.25 ml methyl t-butyl ether. The solution is allowed to stand and the resulting precipitate is filtered and air dried resulting in Form A.

Form A can also be prepared by slurrying 34 mg of amorphous 3-[5-chloro-4-[(2,4-difluorobenzyl)oxy]-6-oxopyrimidin-1(6H)-yl]-N-(2-hydroxyethyl)-4-methylbenzamide in 0.5 ml isopropyl ether. The resulting solid is filtered and air dried resulting in Form A Form A can also be prepared by direct crystallization of amorphous 3-[5-chloro-4-[(2,4-difluorobenzyl)oxy]-6-oxopyrimidin-1(6H)-yl]-N-(2-hydroxyethyl)-4-methylbenzamide in methyl ethyl ketone. 100 mg of 3-[5-chloro-4-[(2,4-difluorobenzyl)oxy]-6-oxopyrimidin-1(6H)-yl]-N-(2-hydroxyethyl)-4-methylbenzamide is dissolved in 1 ml of MEK. Upon recrystallization the material is filtered and air dried resulting in Form A.

Form A can also be prepared by slurry from the following solvents: ethanol, dioxane, tetrahydro furan, and dimethyl formamide.

Example 3

Preparation of Form B

Form B was prepared by the slurry of 185 mg of amorphous 3-[5-chloro-4-[(2,4-difluorobenzyl)oxy]-6-oxopyrimidin-1 (6H)-yl]-N-(2-hydroxyethyl)-4-methylbenzamide in 3 ml of water for 7 days. The solid material was filtered and air dried resulting in Form B.

Form B can also be prepared by slurrying amorphous 3-[5-chloro-4-[(2,4-difluorobenzyl)oxy]-6-oxopyrimidin-1(6H)-yl]-N-(2-hydroxyethyl)-4-methylbenzamide or crystalline Form A in ethanol and water mixtures with a water activity of 0.4 and above.

Example 4

Preparation of Form C

Form C was prepared by slurrying 31 mg of amorphous 3-[5-chloro-4-[(2,4-difluorobenzyl)oxy]-6-oxopyrimidin-1

(6H)-yl]-N-(2-hydroxyethyl)-4-methylbenzamide in 1 ml of water. The resulting solid was filtered and air dried.

The examples herein can be performed by substituting the generically or specifically described reactants and/or operating conditions of this invention for those used in the preceding examples.

In view of the above, it will be seen that the several objects of the invention are achieved. As various changes could be made in the above methods, combinations and compositions of the present invention without departing from the scope of the invention, it is intended that all matter contained in the above description be interpreted as illustrative and not in a limiting sense. All documents mentioned in this application are expressly incorporated by reference as if fully set forth at length.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A crystalline form of 3-[5-chloro-4-[(2,4-difluorobenzyl)oxy]-6-oxopyrimidin-1(6H)-yl]-N-(2-hydroxyethyl)-4-methylbenzamide having an X-ray powder diffraction pattern comprising a peak selected from the group consisting of 11.8±0.2, 13.7±0.2, 15.8±0.2, 21.4±0.2, 21.9±0.2, 26.2±0.2, and 26.9±0.2 degrees 2 theta.

2. A crystalline form of 3-[5-chloro-4-[(2,4-difluorobenzyl)oxy]-6-oxopyrimidin-1(6H)-yl]-N-(2-hydroxyethyl)-4-methylbenzamide having an X-ray powder diffraction pattern comprising a peak selected from the group consisting of 11.8±0.2, 13.7±0.2, 15.8±0.2, 21.4±0.2 and 26.9±0.2 degrees 2 theta.

3. A crystalline form of 3-[5-chloro-4-[(2,4-difluorobenzyl)oxy]-6-oxopyrimidin-1(6H)-yl]-N-(2-hydroxyethyl)-4-methylbenzamide having an X-ray powder diffraction pattern comprising a peak selected from the group consisting of 11.8±0.2, 15.8±0.2 and 26.9±0.2 degrees 2 theta.

4. A crystalline form of 3-[5-chloro-4-[(2,4-difluorobenzyl)oxy]-6-oxopyrimidin-1(6H)-yl]-N-(2-hydroxyethyl)-4-methylbenzamide having a dehydration point prior to 120° C.

5. The crystalline form of claim 4 having an X-ray powder diffraction pattern comprising peaks at 11.8±0.2, 15.8±0.2 and 26.9±0.2 degrees 2 theta.

6. A crystalline form of 3-[5-chloro-4-[(2,4-difluorobenzyl)oxy]-6-oxopyrimidin-1(6H)-yl]-N-(2-hydroxyethyl)-4-methylbenzamide of having an X-ray powder diffraction pattern substantially as shown in FIG. 2.

7. A pharmaceutical composition comprising 3-[5-chloro-4-[(2,4-difluorobenzyl)oxy]-6-oxopyrimidin-1(6H)-yl]-N-(2-hydroxyethyl)-4-methylbenzamide and one or more pharmaceutically acceptable excipients, wherein a detectable amount of the 3-[5-chloro-4-[(2,4-difluorobenzyl)oxy]-6-oxopyrimidin-1(6H)-yl]-N-(2-hydroxyethyl)-4-methylbenzamide is present as Form B crystalline 3-[5-chloro-4-[(2,4-difluorobenzyl)oxy]-6-oxopyrimidin-1(6H)-yl]-N-(2-hydroxyethyl)-4-methylbenzamide, wherein Form B has dehydration point prior to 120° C., and an X-ray powder diffraction pattern comprising peaks at 11.8±0.2, 15.8±0.2 and 26.9±0.2 degrees 2 theta.

8. The pharmaceutical composition of claim 7 wherein at least about 50% of the 3-[5-chloro-4-[(2,4-difluorobenzyl)oxy]-6-oxopyrimidin-1(6H)-yl]-N-(2-hydroxyethyl)-4-methylbenzamide is present as Form B crystalline 3-[5-chloro-4-[(2,4-difluorobenzyl)oxy]-6-oxopyrimidin-1(6H)-yl]-N-(2-hydroxyethyl)-4-methylbenzamide.

9. The pharmaceutical composition of claim 7 wherein at least about 90% of the 3-[5-chloro-4-[(2,4-difluorobenzyl)oxy]-6-oxopyrimidin-1(6H)-yl]-N-(2-hydroxyethyl)-4-methylbenzamide is present as Form B crystalline 3-[5-chloro-4-[(2,4-difluorobenzyl)oxy]-6-oxopyrimidin-1(6H)-yl]-N-(2-hydroxyethyl)-4-methylbenzamide.

10. The pharmaceutical composition of claim 7 wherein the 3-[5-chloro-4-[(2,4-difluorobenzyl)oxy]-6-oxopyrimidin-1(6H)-yl]-N-(2-hydroxyethyl)-4-methylbenzamide present in the composition is substantially phase pure Form B crystalline 3-[5-chloro-4-[(2,4-difluorobenzyl)oxy]-6-oxopyrimidin-1(6H)-yl]-N-(2-hydroxyethyl)-4-methylbenzamide.

11. The pharmaceutical composition of claim 7 wherein the amount of 3-[5-chloro-4-[(2,4-difluorobenzyl)oxy]-6-oxopyrimidin-1(6H)-yl]-N-(2-hydroxyethyl)-4-methylbenzamide present in the composition is between about 0.1 mg to about 1000 mg.

12. The pharmaceutical composition of claim 7 wherein the amount of 3-[5-chloro-4-[(2,4-difluorobenzyl)oxy]-6-oxopyrimidin-1(6H)-yl]-N-(2-hydroxyethyl)-4-methylbenzamide present in the composition is between about 0.1 mg to about 500 mg.

13. A method of treating an inflammatory condition, the method comprising administering to a subject having or susceptible to such condition or disorder a therapeutically or prophylactically effective amount of a pharmaceutical composition comprising the crystalline form of any one of claims 1-6.

14. The method of claim 13 wherein the inflammatory condition is rheumatoid arthritis.

15. The method of claim 13 wherein the inflammatory condition is osteoarthritis.

16. The method of claim 13 wherein the inflammatory condition is asthma.

\* \* \* \* \*